US005877165A

United States Patent [19]
Miura et al.

[11] Patent Number: 5,877,165
[45] Date of Patent: Mar. 2, 1999

[54] BORONATED PORHYRINS AND METHODS FOR THEIR USE

[75] Inventors: Michiko Miura, Hampton Bays, N.Y.; John A. Shelnutt, Tijeras, N. Mex.; Daniel N. Slatkin, Southhold, N.Y.

[73] Assignee: Brookhaven Science Associates, Upton, N.Y.

[21] Appl. No.: 874,548

[22] Filed: Jun. 13, 1997

[51] Int. Cl.$^6$ ............................. A61K 31/69; C07F 5/05
[52] U.S. Cl. ..................... 514/64; 540/145; 424/1.65; 424/9.362; 534/10; 534/14; 534/15; 514/410
[58] Field of Search ................ 540/145; 514/410, 514/64; 424/1.65, 9.362; 534/10, 14, 15

[56] References Cited

U.S. PATENT DOCUMENTS

| | | | |
|---|---|---|---|
| 4,348,376 | 9/1982 | Goldenberg | 424/1 |
| 4,665,897 | 5/1987 | Wong | 424/1.1 |
| 4,783,529 | 11/1988 | Lavalee et al. | 540/145 |
| 4,824,659 | 4/1989 | Hawthorne | 424/1.1 |
| 4,837,221 | 6/1989 | Bonnett et al. | 514/410 |
| 4,959,356 | 9/1990 | Miura et al. | 514/64 |
| 4,992,257 | 2/1991 | Bonnett et al. | 424/9 |
| 5,149,801 | 9/1992 | Kahl et al. | 540/145 |
| 5,194,603 | 3/1993 | Tsuchida et al. | 540/145 |
| 5,236,914 | 8/1993 | Meunier et al. | 514/185 |
| 5,252,698 | 10/1993 | Bhardwaj et al. | 528/230 |
| 5,262,532 | 11/1993 | Tweedle et al. | 540/145 |
| 5,284,821 | 2/1994 | Kahl et al. | 514/21 |
| 5,284,831 | 2/1994 | Kahl et al. | 514/21 |
| 5,314,905 | 5/1994 | Pandey et al. | 514/410 |
| 5,663,328 | 9/1997 | Ellis, Jr. et al. | 568/910 |
| 5,674,467 | 10/1997 | Maier et al. | 424/1.65 |

FOREIGN PATENT DOCUMENTS

| | | |
|---|---|---|
| 59-101488 | 12/1982 | Japan . |
| 4-82889 | 7/1990 | Japan . |
| WO 90/15803 | 2/1990 | WIPO . |
| WO 93/07150 | 10/1992 | WIPO . |

OTHER PUBLICATIONS

Miura et al.,, "Synthesis, Tissue Uptake, and Toxicity of a Nickel Tetracarboranylphenylporphyrin", Paper presented at 6th International Symposium in Neutron Capture Therapy for Cancer, Kobe, Japan (Oct. 31–Nov. 4, 1994).

Miura et al., "Synthesis and Spectroscopic Characterization of Octaacetic Acid Tetraphenylporphyrins", *Inorganic Chemistry*, 33(26)(1994).

Miura et al., "Biodistribution and Toxicity of 2,4–Divinly–Nido–o–Carboranyldeuteroporphyrin IX in Mice", *Biochemical Pharmacology*, 43(3), pp. 467–4(1992).

Miura et al., "Preparation of Carboranyl Porphyrins for Boron Neutron Capture Therapy", *Tetrahedron Letters*, 31(16), pp. 2247–2250 (1990).

Chiusoli et al., "Synthesis of Pyrrole–3,4–diacetic Acid and Its Derivatives", *Synthesis*, pp. 262–265 (1989).

Coderre et al., "Boron Neutron Capture Therapy of Glioblastoma Multiforme Using p–boronophenylalanine and Epithermal Neutrons: Trial Design and Early Clinical Results", *J. NeuroOncol* 33pp. 141–152 (1997).

Coderre et al., "Selective Delivery of Boron by the Melanin Precursor Analogue *p*boronophenylalanine to Tumors Other Than Melanoma", *Cancer Res.*, 50, pp. 138–141 (1990).

Fairchild et al., "Microanalytical Techniques for Boron Analysis Using the $^{10}B(n,\alpha)^7Li$ reaction", *Med. Phys.*, 13, pp. 50–56 (1986).

Miura et al., "Synthesis of a Nickel Tetracarboranylphenylporphyrin for Boron Neutron–Caputure Therapy: Biodistribution and Toxicity in Tumor–Bearing Mice", *Int. J. Cancer:* 68, pp. 114–119 (1996).

Oenbrink et al., "Accumulation of Porphyrins in Cells: Influence of Hydrophobicity, Aggregation and Protein Binding", *Photochem. Photobiol.*, 48, pp. 451–456 (1988).

Slatkin et al., "Biodistribution and Toxicity of 2,4–Divinly–Nido–o–Carboranyl–Deuteroporphyrin IX in Mice, Erratum", *Biochem. Pharm.*, 50, pp. 893–894 (1995).

*Primary Examiner*—Mukund J. Shah
*Assistant Examiner*—Pavanaram K. Sripada
*Attorney, Agent, or Firm*—Margaret C. Bogosian

[57] ABSTRACT

The present invention covers boronated porphyrins containing multiple carborane cages which selectively accumulate in neoplastic tissue within the irradiation volume and thus can be used in cancer therapies such as boron neutron capture therapy and photodynamic therapy.

32 Claims, 3 Drawing Sheets

1, NiTCP, R=CH₂CO₂CH₃, Y=OCH₂C₂B₁₀H₁₀, M=Ni
2, NiTCP-H, R=H, Y=OCH₂C₂B₁₀H₁₀, M=Ni
3, NiNTCP-H, R=H, Y=OCH₂C₂B₉H₁₀-K+, M=Ni
4, CuTCP, R=CH₂CO₂CH₃, Y=OCH₂C₂B₁₀H₁₀, M=Cu

5, NiDPE, R=C₂B₁₀H₁₀, Y=CH₃, M=Ni
6, ZnDPE, R=C₂B₁₀H₁₀, Y=CH₃, M=Zn
7, VCDP, R=C₂B₉H₁₀-K+, Y=H, M=2H

BORONATED PORHYRINS AND METHODS FOR THEIR USE

This invention was made with Government support under contract number DE-AC02-76CH00016, awarded by the U.S. Department of Energy. The Government has certain rights in the invention.

BACKGROUND OF THE INVENTION

The present invention relates to compounds and methods for treating malignant tumors, in particular brain tumors, using such compounds.

Porphyrins in general belong to a class of colored, aromatic tetrapyrrole compounds, some of which are found naturally in plants and animals, e.g., chlorophyll and heme. Porphyrins are known to have a high affinity to neoplastic tissues of mammals, including man. Because of their affinity for neoplastic tissues, in the central nervous system (CNS), porphyrins with boron-containing substituents using boron neutron capture therapy (BNCT) can be useful in the treatment of primary and metastatic tumors. Porphyrins and other tetrapyrroles with relatively long singlet lifetimes can be used to treat malignant tumors via photodynamic therapy (PDT).

In addition, porphyrins can be used in vivo as chelating agents for (1) certain paramagnetic metal ions to achieve higher contrast in magnetic resonance imaging (MRI) or for (2) radioactive metal ions for tumor imaging in single-photon-emission tomography (SPECT) or position emission tomography (PET) and/or in radioisotope-mediated radiation therapy. Thus, appropriately radiolabeled porphyrins can be imaged noninvasively in nuclear medicine employing SPECT or PET.

Boron neutron-capture therapy [BNCT] is a bimodal cancer treatment based on the selective accumulation of a $^{10}B$ carrier in Lumors, and subsequent irradiation with thermalized neutrons. The production of microscopically localized high linear-energy-transfer (LET) radiation from capture of thermalized neutrons by $^{10}B$ in the $^{10}B(n,\alpha^7Li)$ reaction is responsible for the high efficacy and sparing of normal tissues. More specifically, the stable nuclide boron-10 ($^{10}B$) absorbs thermalized neutrons to create ionizing radiation ($^7Li$ and $^4He$) with ranges of 5 and 9 $\mu m$, respectively.

When BNCTI is used in patients with malignant brain tumors, the patient is injected with a boron compound highly enriched ($\geq 95$ atom %) in boron-10. The boronated compound used is one chosen that has the property of concentrating preferentially in the brain tumor within the radiation volume. For some BNCT compounds, the action of the blood-brain barrier slows or prevents their entry into healthy, normal, surrounding central nervous system tissues. The patient's head is then irradiated in the general area of the brain tumor with an incident beam or field of epithermal (0.5 eV–10 keV) neutrons. These neutrons become progressively thermalized (average energy$\approx 0.04$ eV) as they penetrate deeper into the head. As they become thermalized, they can more readily be captured by the boron- 10 concentrated in the tumor cells and/or tumor supporting tissues. A small proportion of the boron-10 nuclei in and around a tumor undergo a nuclear reaction immediately after capturing a neutron which produces the high LET alpha ($^4$ He) and lithium ($^7Li$) particles. The tumor in which the boron-10 was concentrated is thus irradiated by these short range particles, which, on average travel a distance comparable to or slightly less than the diameter of a typical tumor cell. Therefore, a very localized, specific reaction takes place whereby the tumor receives a large radiation dose compared with that received by surrounding non-neoplastic tissues, with relatively low boron-10 concentrations.

For BNCT of malignant brain tumors, it is particularly important that there be robust uptake of boron in tumor relative to normal tissues (i.e., blood and normal brain tissues) within the neutron-irradiated target volume. BNCT has been used clinically at the Brookhaven National laboratory Medical Department using p-boronophenylalaninc [BPA] as the boron carrier (Coderre, et al., 1997). BPA has the outstanding quality of not eliciting any chemical toxicity associated with its usage. However, because the brain and blood boron concentrations are approximately one-third that found in tumor, the tumor dose is restricted. In order to improve upon the currently used boron delivery agent, BPA, it has been postulated that tumor boron concentrations should be greater than 30 $\mu g$ B/g and tumor:blood and tumor:brain boron ratios should be greater than 5:1 (Miura, et al., 1996).

In PDT of malignant tumors using porphyrins, the patient is injected with a photosensitizing porphyrin drug. The drug localizes preferentially in the tumor within the irradiation volume. The patient's tissues in the zone of macroscopic tumor is then irradiated with a beam of red laser light. The vascular cells of the irradiated tumor and some of the tumor cells are rendered incapable of mitotic activity or may be rendered nonviable outright if the light penetrates the tissue sufficiently. The biochemical mechanism of cell damage in PDT is believed to be mediated largely by singlet oxygen. Singlet oxygen is produced by transfer of energy from the light-excited porphyrin molecule to an oxygen molecule. The resultant singlet oxygen is highly reactive chemically and is believed to react with and disable cell membranes. Macroscopically, there appears to be some direct damage to tumor cells, extensive damage to the endothelial cells of the vasculature, and infiltration of the tumor by macrophages. The macrophages remove detritus of dead cells from the PDT-treated zones of tissue, and in the process, are believed to damage living cells also.

In PDT, the porphyrins must be selectively retained by tumors, especially within the irradiation volume. However, the porphyrin drugs should be non-toxic or minimally toxic when administered in therapeutically useful doses. In addition, the porphyrin drugs must have absorbance peaks at long wavelengths to allow increased tissue penetration and, thereby, allow photoablation of some or all of the vasculature and/or parenchyma of deep-seated tumors.

While it is well known in medical arts that porphyrins have been used in cancer therapy, there are several criteria that must be met for a porphyrin-mediated human cancer radiation treatment to be optimized. In BNCT, the porphyrin drug should deliver a therapeutically effective concentration of boron to the tumor while being minimally toxic to normal tissues and organs at a radiotherapeutic effective pharmacological whole-body dose of porphyrin. In addition, the porphyrin should have selective affinity for the tumor with respect to its affinity to surrounding normal tissues within the irradiation volume, and should be capable of achieving tumor-to-normal-tissue boron concentration ratios greater than 5:1. We show here on the basis of in vivo studies that the latter criterion can be satisfied for brain tumors if the porphyrin, properly designed, synthesized and purified, does not penetrate the blood-brain-barrier in non-edcmatous zones of the normal CNS.

In addition, if the boron concentration and distribution in and around the tumor could be accurately and rapidly determined noninvasively, BNCT treatment planning could be more quickly, accurately, and safely accomplished. For example, this could enable neutron irradiation to be planned so that concurrent boron concentrations are maximum at the growing margin of the tumor rather than in the tumor as a whole. Thus, BNCT could be implemented by one relatively short exposure or a series of short exposures of mainly epithermal neutrons, appropriately timed to take advantage of optimal boron concentrations identified by SPECT or MRI in tumor, surrounding tissues, and blood in vivo. BNCT effectiveness in vivo is probably not diminished even when a neutron exposure is as short as 300 milliseconds. Such short irradiations have been delivered, in fact, by a TRIGA (General Atomics) reactor operating in the pulse mode. The inconvenience and discomfort to the patient of long and often awkward positioning of the head at the reactor port could be thereby ameliorated. Even this advantage alone would justify a clinical use for BNCT, if palliative results on the tumor were at least as favorable as those following the presently, available standard, 6-week, 30-fraction postoperative photon radiation therapy.

Efforts have been made to synthesize porphyrins for the diagnosis, imaging and treatment of cancer. In U.S. Pat. No. 4,959,356 issued to Miura, et al., a particular class of porphyrins was synthesized for utilization in the treatment of brain tumors using BNCT. The porphyrins described in that patent are natural porphyrin derivatives which contain two carborane cages at the 3 and 8 positions. Natural porphyrins have particular substitution patterns which are, in general, pyrrole substituted and are asymmetric. The porphyrins described in U.S. Pat. No. 4,959,356 use heme, the iron porphyrin prosthetic group in hemoglobin, as a chemical starting material; therefore, the resulting boronated porphyrins resemble heme in their basic structure. In contrast, the porphyrins of the current invention are synthetic tetraphenylporphyrin (TPP) derivatives that are symmetrically substituted at the methine positions and most are also substituted at the pyrrole positions of the macrocycle. Acyclic precursors are used as chemical starting materials so that final product yields are generally greater than those obtained from natural porphyrin derivatives.

U.S. Pat. Nos. 5,284,831 and 5,149,801 issued to Kahl, et al. describe another type of porphyrin and their uses in BNCT, PDT and other biomedical applications. Like the porphyrins described in the previous patent by Miura et al., these are also natural porphyrin derivatives but they contain four carborane cages at the 3 and 8 positions.

U.S. Pat. No. 4,500,507 issued to Wong describes a method of labeling hematoporphyrin derivatives (HPD) with $^{99m}$Tc as a means of visualizing tumors using scintigraphic noninvasive imaging techniques such as SPECT. The method taught by this patent utilizes hematoporphyrin compounds that are also natural porphyrin derivatives.

U.S. Pat. Nos. 4,348,376 to Goldenberg, 4,665,897 to Lemelson, and 4,824,659 to Hawthorne teach combining labeling of an antibody with $^{10}$B and with one or more other radionuclides, including those of iodine, for purposes of imaging tumors noninvasively and thereby delineating tumor targets for exposure to thermalized neutrons. Each of these patents requires that the $^{10}$B compound be linked to a radiolabeled antibody.

It is, therefore an object of the present invention to describe a new class of non-toxic boronated porphyrin compounds used with or without ancillary substances such as antibodies. It is also an object of the present invention to provide methods for their use in treating tumors, for example, malignant brain tumors.

An additional objective of the present invention is to provide methods of utilizing any one or more of this new class of boronated porphyrins containing four carborane cages and a central metal ion to localize, analyze, and treat malignant tumors, for example, brain tumors. A further object of the present invention is to provide methods for treating malignant tumors in general using these new boronated porphyrins using BNCT and/or PDT.

Another object of the present invention is to provide a method for directly and noninvasively imaging and quantifying boron concentrations in tissues using the compounds of the present invention via SPECT, PET and/or MRI, thereby permitting rapid enhanced targeting and planning of subsequent neutron irradiation of those tissues.

SUMMARY OF THE INVENTION

The present invention covers new boronated porphyrins of formula I:

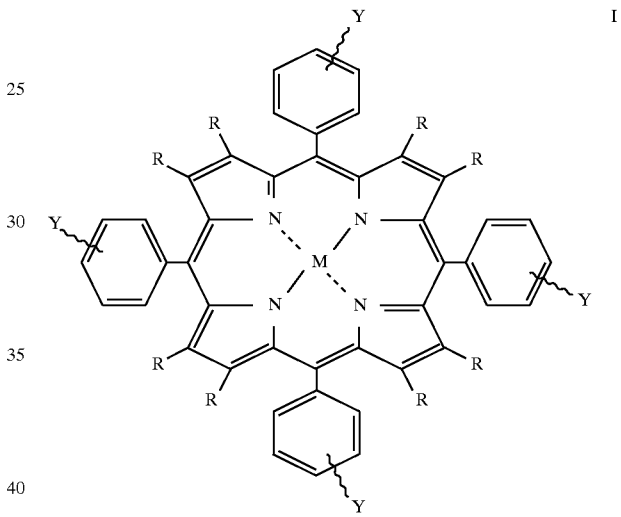

wherein M is 2H, a radiometal imageable by SPECT and PET techniques or a paramagnetic metal that could be detected by MRI technique or a metal useful in radioisotope-mediated radiation therapy, via BNCT and PDT; R is alkyl or $(CH_2)_nCOOZ$ when M is a metal; R is H, alkyl or $(CH_2)_nCOOZ$ when M is 2H, wherein n is an integer between 0 and 20, Z is selected from the group consisting of H, alkyl, or aryl; and Y is selected from the group consisting of ortho, meta or para $O(CH_2)_nC_2HB_9H_{10}$ or $O(CH_2)_nC_2HB_{10}H_{10}$ wherein n is as defined above, $C_2HB_9H_{10}$ is nido ortho-carborane, meta-carborane or para-carborane and nido ortho-carborane has the formula

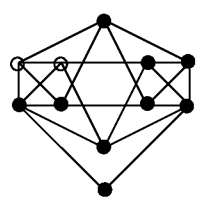

and $C_2HB_{10}H_{10}$ is ortho-carborane, meta-carborane or para-carborane, of formula

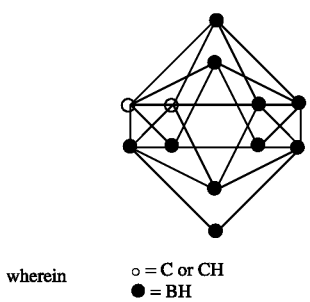

wherein  o = C or CH
● = BH

In a preferred embodiment of the compounds of formula I, M is selected from the group consisting of Cr, Mn, Fe, Co, Ni, Cu, Zn, Tc, In, Sn, Pt, Gd and yttrium, R, Z and Y of Formula I remaining as described above.

The present invention further covers new boronated porphyrins of the formula

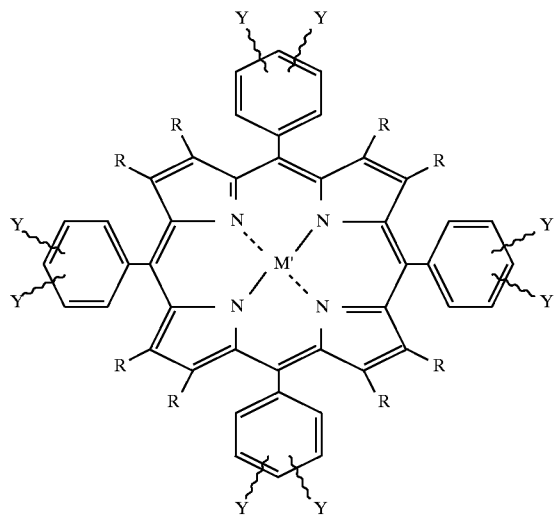

II wherein $M^1$ is 2H, 4H, an imageable radiometal which can be imaged by SPECT or PET techniques, a paramagnetic metal which can be detected by MRI or a metal useful in radioisotope-mediated radiation therapy, BNCT, and/or PDT. R and Y were defined above.

In another preferred embodiment of the compounds of formula I, Z is alkyl. In yet another preferred embodiment, M is Ni, R is $CH_2CO_2Z$, Z is methyl, and Y is $OCH_2C_2HB_{10}H_{10}$, producing nickel tetracarboranylphenylporphyrin (NiTCP).

In formula I or II alkyl is an unsubstituted straight chain or branched alkyl having 1 to 20 carbon atoms, aryl is unsubstituted phenyl, naphthyl or phenanthryl.

The present invention also relates to a method of treating malignant tumors which includes administering to a person in need of such treatment a sufficient dosage of the compound selected from those set forth above.

In one preferred embodiment, the method of treating malignant tumors of the present invention is via boron neutron capture therapy (BNCT).

In another preferred embodiment, the method of treating malignant tumors of the present invention is via photodynamic therapy (PDT).

In another preferred embodiment, the method of imaging malignant tumors of the present invention is through the use of SPECT when M is a SPECT-imageable radiometal.

In another preferred embodiment, the method of imaging malignant tumors of the present invention is through the use of MRI when M is any paramagnetic metal in the Periodic Table of Elements.

In another preferred embodiment, the method of treating malignant tumors of the present invention utilizes SPECT to (1) noninvasively visualize and (2) directly quantify boron concentrations in tissue, thereby permitting rapid enhanced targeting and planning of neutron irradiation of tumors in BNCT when M is a SPECT-imageable radiometal. This permits rapid enhanced targeting and treatment-planning for neutron irradiation in BNCT during the infusion of the boronated compound and during the postinfusion period before exposure to neutrons when the compound is being redistributed in the blood, brain, and brain tumor tissues.

In another preferred embodiment, the method of treating malignant tumors of the present invention utilizes MRI to (1) noninvasively visualize and to (2) directly quantify boron concentrations in tissue, thereby permitting rapid enhanced targeting and planning of neutron irradiation of tumors in BNCT when M is a paramagnetic metal that is MRI-imageable.

A conceptual and practical advantage of the present invention over the prior art for the treatment of cancer is that the boronated porphyrins of the invention can selectively accumulate in neoplasms and can allow selective destruction of tumor tissue with minimal disruption of normal tissues and tissue function when irradiated with either thermalized neutrons for BNCT or visible light for PDT. The tumor cells and/or tumor vasculature are destroyed without side effects as serious as those observed in patients after conventional therapies, such as photon radiotherapy or chemotherapy. This sparing of normal tissues occurs without the thrombocytopenia caused by all other classes of presently known, so tested boronated porphyrins. Thrombocytopenia, even if induced transiently by a reversible pharmacological effect, would be a critically important toxicity caused by a BNCT compound particularly if used to treat a patient with a malignant brain tumor. This is because such patients are deemed to be more prone to cerebral hemorrhage than are individuals of the same age with similar cardiovascular status without malignant brain tumors.

Another advantage of the present invention is to provide porphyrin compounds for BNCT or PDT that are active at lower doses of injected material as compared with porphyrins known presently in the art of cancer treatment by BNCT or PDT.

For a better understanding of the present invention, reference is made to the following description taken in conjunction with the examples, the scope of which is set forth in the appended claims.

DETAILED DESCRIPTION OF THE INVENTION

Figure 1:
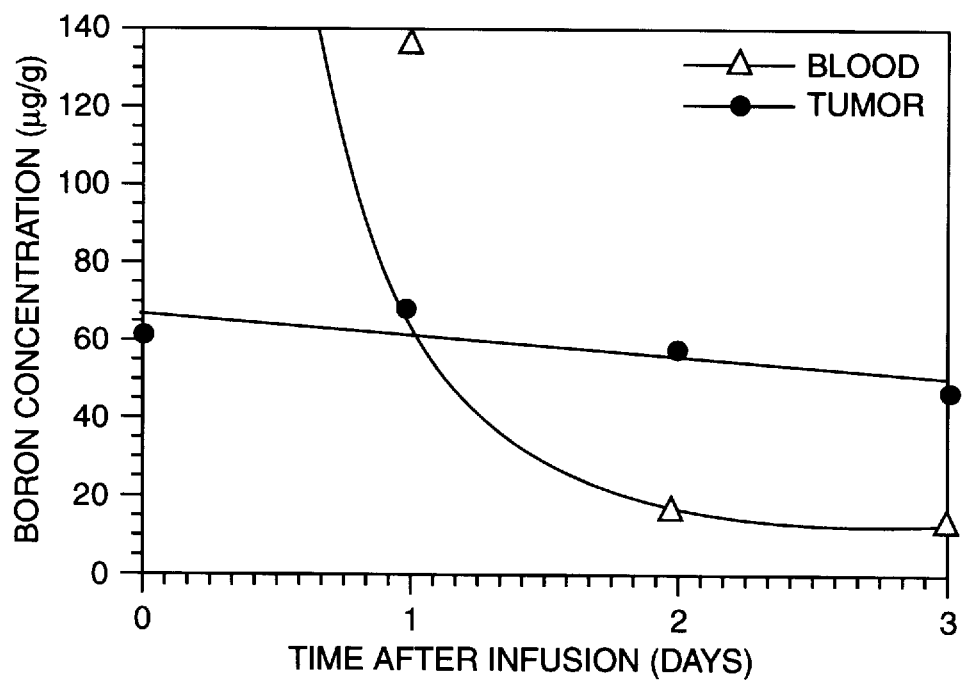
FIG. 1 illustrates boron uptake by Fischer 344 rats bearing 9L gliosarcomas given approximately 215 mg CuTCP/kg by a 48 hour intravenous (i.v.) infusion as it varies with time.

The boronated porphyrins of the present invention can be synthesized using Lindsey's cyclization method (Miura, et al. 1996). The following reaction Scheme I depicts the synthesis of the compounds of Formula I.

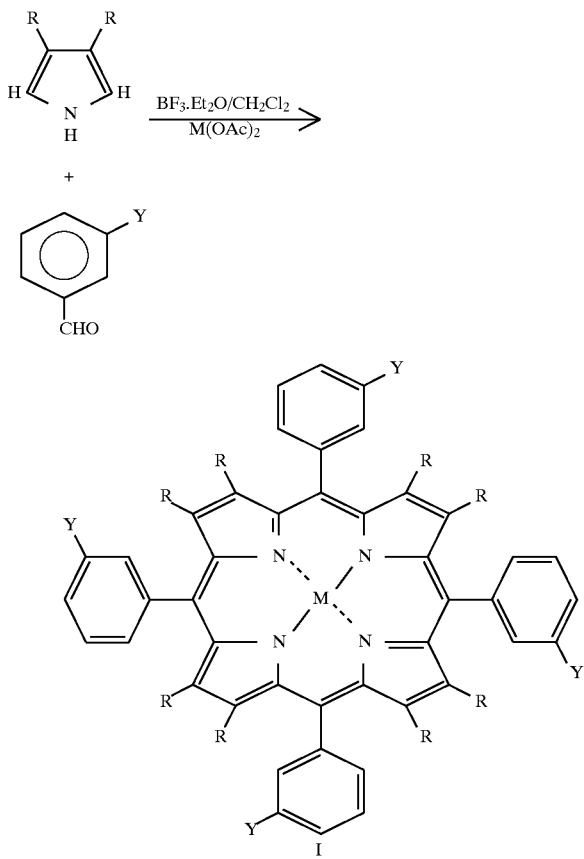

Synthesis of pyrrole esters where Z is not $CH_3$ requires that the precursor, benzoyldipropargylamine, be treated with another alcohol besides methanol in the reductive carbonylation step using potassium iodide and palladium/carbon (Chiusoli et al., 1989). Alternatively, pyrrole-3,4-diacetic acid (Chiusoli, et al. 1989) can be esterified with the desired alcohol using standard methods e.g., thionyl chloride or carbonyldiimidazole.

The same basic approach shown in reaction scheme 1 can also be used for the preparation of the compounds of formula II by using dihydroxybenzyl alcohol as a starting material instead of 3-hydroxybenzyl alcohol used in the synthesis of NiTCP.

Preferred compounds of the present invention contain four carborane cages and a central metal ion. Because the macrocycle is highly substituted (when R≠H), it is sterically hindered and has adopted a nonplanar conformation. In comparison to planar porphyrins, the aromaticity of the porphyrin is reduced and therefore the basicity of the nitrogens is increased. Thus, in the metal-free porphyrin, all four of the core nitrogens are protonated at neutral pH forming a dication which has an indicative optical absorption spectrum. For example, when the intermediate porphyrinogen (formed from the initial reaction between pyrrole and benzaldehyde) is oxidized with dichlorodicyanobenzoquinone (DDQ), a porphyrin dication is formed in a neutral, aprotic solvent such as dichloromethane.

The percentage of boron by weight for the compounds of the present invention varies with the particular porphyrin, but, as an example, unenriched, natural boron-containing NiTCP is 22.3% boron by weight whereas unenriched NiTCP-H (FIG. 2) is 31.8% boron by weight.

The porphyrin compounds of the present invention that have been tested in vivo are non-toxic at theoretically therapeutic effective doses. Implementation of BNCT and/or PDT in animals and patients so dosed could selectively destroy tumor tissue without disruption of normal tissue function when irradiated with epithermal neutrons or laser light. The tumor destruction could occur without the serious side effects that may be observed in conventional tumor therapy, such as radiotherapy or chemotherapy.

The porphyrin compounds of the present invention can be employed as vehicles for the transport of boron to malignant tumors, especially brain tumors. The blood-brain barrier [BBB] in mammals excludes the uptake of boronated porphyrins of the present invention into normal brain tissues while allowing access of the porphyrins to tumor cells and tissues where the BBB is entirely or partially destroyed. Moreover, the permeability and/or accessibility by other mechanisms of the porphyrins to the cytoplasm of neoplastic cells across the plasma membrane evidently favors robust concentrations of the porphyrin in such cells, even when the cells are exposed to relatively low concentrations of porphyrin in their environment, whether edematous or not.

The present invention also includes a method of treating malignant brain tumors that comprises administrating to a person deemed in need of such treatment a sufficient dosage of the compound selected from those set forth above.

In a preferred embodiment, the method of treating malignant tumors, especially brain tumors, is via BNCT.

BNCT is an anticancer bimodal radiation therapy which utilizes the ability of the stable, non-radioactive nuclide boron-10 ($^{10}B$) to absorb preferentially thermalized neutrons. In BNCT of malignant brain tumors following the method of the present invention, the patient is first given an infusion of a boronated porphyrin of formula I or formula II, which is highly enriched in the $^{10}B$ isotope. The boronated porphyrin is then concentrated preferentially in the brain tumor within the effective irradiation volume, which, for brain tumors may be a substantial part of the brain. For example, tumors in most of one hemisphere or all of one hemisphere and some or all of the contralateral hemisphere of the brain could accumulate boronated porphyrins. The tumor area is then irradiated with thermalized neutrons (primary irradiation), some of which are captured by the boron-10 concentrated in the tumor. The relative probability that the slow-moving thermal neutrons will be absorbed by the boron-10 nuclide is high compared to the probability of absorption by all of the other nuclides normally present in mammalian tissues, provided that $^{10}B$ concentrations in tumor tissues is greater than 30 μg/g.

Boron-10 undergoes the following nuclear reaction when captured by a thermal neutron:

$$^{10}B + n \rightarrow *^{11}B,$$

$$*^{11}B \rightarrow ^{7}Li + ^{4}He + \gamma (478 \text{ keV})$$

In this nuclear reaction, a $^{10}B$ nucleus absorbs a neutron, forming the metastable nuclide $*^{11}B$, which spontaneously and nearly instantaneously disintegrates into a $^{4}He$ and a $^{7}Li$ particle, which together possess an average total kinetic energy of 2.34 MeV. These two ionized particles travel about 9 μm and 5 μm in opposite directions in soft tissue, respectively. Accordingly, the high LET particles have a high probability of rendering non-clonogenic any mitotically active or potentially active cell such as a cancer cell, and/or a cell of the blood vessels in the tumor that allow the cancer to grow, the nucleus of which intersects the trajectory of either of the two particles. In effect, the tumor alone is preferentially irradiated with these high LET alpha and $^7$Li particles, the ranges of which in tissue are 7±2 μm, distances comparable to the diameter of many tumor and tumor-associated cells. Therefore, the efficacy of BNCT resides in the production of highly localized, high LET ionizing radiation within the targeted tissues. In this manner, the tumor can receive a preferentially large radiation dose compared to that received by the surrounding and contiguous non-cancerous tissue. Optimally, the preferential accumulation of boron-10 in the tumor permits the radiation dose to the tumor to exceed substantially the dose to the blood vessels of the surrounding normal brain and the extravascular normal brain tissue.

Currently, the compounds of the present invention are being investigated in animals and in other preclinical studies at Brookhaven National Laboratory with a view toward their use in future postoperative treatment of patients with glioblastoma multiforme, a highly malignant brain tumor. The compounds of the present invention are intended to be utilized for BNCT, which is based on the $^{10}B(n,\alpha)^7Li$ reaction whereby high LET radiation results from the reaction between $^{10}$B and thermal neutrons.

To accumulate the requisite amount of a compound of the present invention in a tumor, generally a systemically injected or infused dose of about 10–50 mg $^{10}$B per kg body weight in a pharmaceutically acceptable carrier would be administered to a patient. Such a carrier includes commercially available solvents, such as Cremophore EL, propylene glycol, Tween 80, or liposomes. The compound is administered in one or more doses, the last dose being given between about 1 hour and one week prior to the epithermal neutron irradiation. The long retention time of any of the presently invented compounds would also permit a series of such irradiations in a so-called "fractionated irradiation schedule". Such a schedule is deemed to be advantageous in sparing damage to normal tissues in conventional photon radiation therapy. The quantity of the boron compound used in any particular treatment depends on, among other factors, the boron-10 concentration delivered to tumor and the toxicity of the compound at doses that are therapeutically useful. The timing of the neutron exposure depends upon the concentration in blood, which decreases more rapidly with time than does the tumor concentration. The timing of the administration of the compound will depend on various considerations that are well known to those skilled in the art of clinical BNCT, including the pharmacokinetic behavior of the compound, (e.g., the rate of absorption of the compound into the tumor and into the tumor vasculature) and the rate of excretion from and/or metabolism of the compound in the various tissues that absorb the compound patient. If one of the compounds disclosed in this invention were used for BNCT, SPECT or MRI of the brain, it could not only improve radiation treatment planning for "single-fraction" BNCT, but could also greatly improve such planning for "multiple-fraction" BNCT, when delivered in a manner consistent with the known pharmacokinetics of the compound, in a quantity sufficient for BNCT of the targeted neoplasm.

In another preferred embodiment, the method of treating malignant tumors of the present invention is via PDT. PDT is another bimodal cancer treatment which combines a photosensitizing compound with red light, to destroy tumor tissue in preference to surrounding normal tissue. In PDT, using the present invention, the patient would first be given an injection or infusion of a photosensitizing boronated porphyrin of formula I or formula II. Fiber-optic probes can then be used to illuminate the tumor tissue. When these tissues that contain photosensitizer are exposed to red light in the presence of oxygen, singlet oxygen is produced which can destroy the tumor without disrupting the surrounding normal tissues that do not contain the photosensitizer.

Upon activation with light, an electron of the porphyrin is excited from the singlet ground state to a singlet excited state. The electron then can either return to the singlet ground state with the emission of light causing fluorescence, or it can change its spin via intersystem crossing to the triplet state. In the decay of the triplet back down to the ground state singlet, it can transfer energy to ground state triplet dioxygen which forms the highly reactive singlet oxygen. Biomolecules that react most readily with singlet oxygen include unsaturated lipids and α-amino-acid residues, both of which are major constituents of biological membranes. Beyond a certain reversible or repairable threshold, damage to membranes, especially to endothelial cell membranes, can lead to local vascular thrombosis and shutdown of blood circulation. This chain of events is believed to be a major factor in the inhibition or cessation of tumor growth by PDT.

For malignant tumors, it is preferable that the PDT photosensitizers have optical absorbance peaks at sufficiently long wavelengths to allow penetration to the depth of the tumor.

In SPECT scanning for BNCT, the patient is first given an infusion or injection of a compound of formula I or of formula II wherein M or $M^1$ is a radiometal. The patient's head is then scanned noninvasively and the radionuclide concentration (and thereby indirectly, the boron concentration) in each pixel or voxel representing brain or brain tumor tissue can not only be imaged but also be represented by an average boron concentration. Contour lines representing zones of equal $^{10}$B concentration can thereby be drawn on each image of the brain.

SPECT of the brain is not only at least one order of magnitude more sensitive to isotopic tracers than is conventional radiography or computerized tomography, but conventional radiographs could not be analyzed with sufficient rapidity so as to provide quantitative information, in defined volumes or voxels of the brain images, about the concentrations of boron of relevance to BNCT treatment planning and implementation. This technique with this new class of porphyrins is based on computer analysis of the absorption of finely collimated, coarsely collimated, or even noncollimated photons that project from the tumor and from the brain to the photon detector or detectors from numerous angles. SPECT scanning can indicate the presence of a tumor in the patient, as well as its location in the brain or elsewhere in the body. SPECT scanning is preferred particularly for this invention because it is noninvasive, fast, widely available, less costly, and more convenient than PET.

In another preferred embodiment, the method of treating malignant tumors of the present invention is through the use of MRI.

In MRI, a patient can first be given an infusion or injection of a solution containing a compound of the present invention with a chelated paramagnetic metal ion for higher contrast. For a brain tumor, the patient's head is then scanned and the paramagnetic metal ion concentration and thus boron concentration in the brain can be imaged. Consequently, the visualized boron concentration can be rapidly quantified. The boron containing compounds of the present invention can be utilized in MRI because they can chelate paramagnetic metal ions. Thus, the compounds of the present invention allow visualization of the paramagnetic metal ion concentration and therefore the boron concentration can be rapidly imaged and quantified.

In addition, since the compounds of the present invention can allow imaging and quantification of paramagnetic metal ion concentration and indirectly thereby the boron-10concentration since, for stable chelation in vivo, the ratio of boron to metal is constant, they can play a significant role in treatment-planning for neutron irradiation in BNCT. More specifically, MRI utilizing the compounds of the present invention permits rapid enhanced targeting and treatment planning for neutron irradiation in BNCT during the infusion and postinfusion period of the boronated compound, when the boronated compound is being redistributed in blood, tumor, and healthy tissue before, during and after neutron exposure.

EXAMPLES

Examples have been set forth below for purpose of illustration and to describe the best mode of the invention at the present time. The scope of the invention is not to be in any way limited by the examples set forth herein.

Example 1

Synthesis of NITCP, CuTCP, MnTCP, CuTCP-H

In this example, Nickel Tetracarboranylphenylporphyrin (NiTCP), Copper Tetracarboranylphenylporphyrin (CuTCP) and Manganese Tetracarboranylphenylporphyrin (MnTCP) and Copper Tetracarbonylphenyl porphyrin hydride (CuTCP-H) were prepared.

1A. Synthesis of Nickel Tetracarboranylphenylporphyrin (NiTCP)

A boronated porphyrin of the present invention, NiTCP, was synthesized using Lindsey's cyclization method as shown in Reaction Scheme 1. Pyrrole-3,4-diacetic acid dimethyl ester (prepared according to Chiusoli et al., 1989) in the amount of 79 mg and 3-o-carboranylmethyloxybenzaldehyde (prepared according to Miura et al., 1990) in the amount of 91 mg were dissolved in 20 ml of $CH_2Cl_2$ and then deoxygenated with nitrogen ($N_2$) for 20 minutes. 15 $\mu$l of $BF_3.Et_2O$ was added and then allowed to stir at 25° C. under $N_2$ for approximately 1.5 hours to form an intermediate porphyrinogen.

This porphyrinogen was then oxidized in situ with dichlorodicyanobenzoquinone (DDQ) and a porphyrin dication was formed. The reaction progress was monitored by optical absorption spectroscopy.

After removal of all volatile components, the reaction mixture was dissolved in chloroform ($CHCl_3$) and then treated with a nickel acetate/methanol solution at reflux for about 2 hours, until nickel insertion was complete. NiTCP was purified by affinity chromatography using silica as solid support and dichloromethane as eluent.

NiTCP gave the following proton nuclear magnetic resonance (NMR) spectrum (in $CDCl_3$): 7.8–7.2 (m, 16H, ArH); 4.59(s,8H, $CH_2B_{10}H_{10}$); 4.16 (s,4H, $B_{10}H_{10}CH$); 3.36 (s,24H, $OCH_3$); 3.26 (s, 16H, $CH_2CO_2Me$); 3.5–1.0 (br. s, 40H, $B_{10}H_{10}$). UV-vis $(CH_2Cl_2)\lambda_{max}$ (nm) 438,555,594. MS FAB for $C_{80}H_{108}N_4O_{20}B_{40}Ni$(m/e) 1935 (M-1).

NiTCP was then emulsified with cremophor (CRM), propylene glycol (PrG) and saline solution to be utilized in preclinical experiments for BNCT.

1B. Synthesis of Copper Tetracarboranylphenylporphyrin (CuTCP)

Another boronated porphyrin of the present invention, CuTCP was prepared using the same procedure as that for NiTCP except that after the oxidation step and removal of volatile components, the reaction mixture was dissolved in chloroform and treated, while refluxing, with a saturated solution of Cu(II) acetate in methanol. The reaction progress was monitored by optical absorption spectroscopy. When copper insertion was complete, the reaction mixture was diluted with dichloromethane, washed with water and dried over anhydrous $Na_2SO_4$. The solvents were removed in vacuo and CuTCP was purified by flash chromatography ($SiO_2$) using 1% acetone in dichloromethane as the eluent. CuTCP had the following spectral characterization data:

$^1$H-NMR ($CDCl_3$): 6.60–7.26 (m, 16H, ArH); 4.43 (br s, 8H, $CH_2O$); 4.11 (br s, 14H, carborane CH); 3.42 (br s, 15H, $OCH_3$); 1.2–3.4 (m, 40H, BH) UV-Vis $(CH_2Cl_2)\lambda_{max}$ (nm) 436, 452 (sh), 573.

1C. Synthesis of Manganese Tetracarboranylphenylporphyrin (MnTCP)

MnTCP was prepared according to the same procedure as CuTCP except that Mn(III) acetate was used instead of Cu(II) acetate. MnTCP was purified by flash chromatography using a $SiO_2$ column with 5–10% acetone in dichloromethane as the eluent. MnTCP had the following spectral characterization data:

UV-Vis $(CH_2Cl_2)\lambda_{max}$ (nm) 374, 497, 602, 650.

1D. Synthesis of Copper Tetracarboranylporphyrin Hydride CuTCP-H

CuTCP-H was prepared by the copper insertion procedure described in Example 1B except that TCP-H was used as the metal-free reactant instead of TCP (Miura el al., 1990). The copper porphyrin was purified by flash chromatography using 1:1 dichloromethane:hexanes as eluent and silica as the solid support. CuTCP-H had the following spectral characterization data:

NMR ($CDCl_3$): 7.10–7.60 (m, 16H, ArH); 4.43 (br. s, 8H, $CH_2O$); 4.11 (br. s, 4H, carborane CH); 1.0–3.3 (br. m, 40H, BH). UV-vis $(CH_2Cl_2)\lambda_{max}$ (nm): 415, 535.

Example 2

Preparation of Boronated Porphyrin Solutions

In this example, solutions of the different boronated porphyrins synthesized in Example 1 were prepared.

2A. Preparation of NiTCP Solution 111 mg of NiTCP was dissolved in 2.2 milliliter (ml) of CRM and 4.4 ml of propylene glycol (PrG) to form a solution.

60 ml of saline was added dropwise to the solution to yield a resulting solution of 1.67 mg NiTCP per ml, 3% CRM and 6% PrG. The injection volume was 0.02 ml/g body weight/injection.

The NiTCP solution was then utilized for biodistribution and toxicity experiments in mice.

2B. Preparation of CuTCP and MnTCP Solution

CuTCP and MnTCP as prepared in Example 1B and 1C were formulated with 6% CRM and 12% propylene glycol (PrG) to form a solution to which saline was added dropwise to yield 1.86 mg/ml of CuTCP and 1.45 mg/ml of MnTCP, respectively. The resulting total doses were 223 mg/kg body weight for CuTCP and 174 mg/kg body weight for MnTCP. These solutions were then utilized for biodistribution and toxicity experiments in mice.

2C. Preparation of CuTCP and CuTCP-H Solution for Rat Studies

CuTCP-H as prepared in Example 1D was formulated with 9% CRM and 18% PrG to form a solution to which saline was added dropwise to yield 3.34 mg/ml of CuTCP and 3.9 mg/ml CuTCP-H, respectively. The resulting total doses were 215 mg/kg body weight for CuTCP and 149 mg/kg body weight for CuTCP-H. These solutions were then utilized for toxicity and biodistribution experiments in rats.

Example 3

Materials and Methods Used for Biological Studies, Chemical and Boron Analysis

3A. Preparation of Animals

Female BALB/c mice (Taconic Farms, Germantown, N.Y.) (20–25 g) were implanted with either KHJJ or EMT-6 tumors. For KHJJ tumors, 1–3 $mm^3$ tumor fragments were implanted subcutaneously (s.c.) in the dorsal thorax of each mouse using an 18-gauge trocar. For EMT-6 tumors, 2.5×$10^5$ cells were implanted similarly using a 27-gauge needle. EMT-6 tumor cells were grown alternately in vivo and in vitro. Single-cell suspensions were prepared from mouse-grown tumors by trypsinization. These were grown in cell culture for several passages and then were frozen in 10% DMSO and stored in liquid nitrogen. Prior to implantation in mice, the cells were thawed and grown in tissue culture in Alpha-MEM with 10% FBS for several passages.

Under deep halothane anesthesia leading to euthanasia, right ventricular blood was collected in Microtainer (Becton-Dickinson, Rutherford, N.J.) tubes containing EDTA for hematological analyses and boron assays of whole blood and in Microtainer™ tubes containing lithium heparin for chemical analyses and enzyme assays of blood plasma. Tumor, brain, fat, muscle, and liver tissues were sampled at necropsy for boron analyses.

3B. Chemical Analysis of Blood Samples

Levels of glucose [GLU], blood urea nitrogen [BUN], blood creatinine [BCR], alanine transaminase [ALT], aspartate transaminase [AST], alkaline phosphatase [ALP], total protein [TPR], albumin [ALB], and creatine phosphokinase [CPK] were determined in blood plasma using a Cobas Fara II microanalysis system. Blood platelets [PLT] and white blood cells [WBC] were counted using a Serono-Baker System 9000 automated hematology microanalyzer.

3C. Boron Analysis of Tissues

Direct current plasma-atomic emission spectroscopy [DCP-AES] (ARL/Fisons Model SS-7) was used (detection limit: 0.1 $\mu$g/ml). Samples (50–130 mg) were digested at 60° C. with sulfuric acid:nitric acid (1:1). Triton X-100 and water were added to give final concentrations of ≈50 mg tissue/ml, 15% total acid v/v and 5% Triton X-100 v/v. Fat and liver tissues were assayed for $^{10}B$ by prompt-gamma spectroscopy (Fairchild, et al., 1986). The prompt-gamma measurements were multiplied by 5.0 to give the total boron concentrations due to the use of boron of natural isotope abundance in the syntheses of all boronated porphyrins reported.

Example 4

Biological Studies Utilizing Control Samples of a Conventional Boron Compound (BPA)—6 hours Seven mice having KHJJ mammary carcinomas were given one intraperitoneal (i.p.) injection of 900 $\mu$g/g body weight of the boron compound presently used for BNCT of malignant brain tumors, p-boronophenylalanine (BPA) complexed with fructose. BPA was prepared in accordance with procedure described in Coderre, et al., 1996 incorporated herein by reference in its entirety as if set forth in full.

Six hours after mice were injected with BPA, right ventricular blood was collected from each mouse for hematological and chemical analysis.

Mice were euthanized during the collection of blood while under Halothane anesthesia. At necropsy, the apparent states of structural integrity, consistency, color or abnormality, if any, of tissues were observed and tumor, brain and liver tissues were collected from each mouse for boron analysis. Results relating to toxicity and efficacy of BPA are set forth in Table 1.

Example 5

Biological Studies Utilizing NiTCP—6 hours

Eight mice having KHJJ mammary carcinomas were injected with the NiTCP solution in the amount of 160 $\mu$g NiTCP/g body weight (36 $\mu$gB/g body weight) in six i.p. injections over 20 hours.

Six hours after the mice were last injected with NiTCP, mice were euthanized during the collection of blood while under Halothane anesthesia and right ventricular blood was collected from each mouse for hematological and chemical analysis without pooling the samples. At necropsy, the apparent states of structural integrity, consistency, color, or abnormality, if any, of tissues were observed and tumor, brain and liver tissues were collected from each mouse for boron analysis without pooling the samples. Results relating to toxicity and efficacy of NiTCP are set forth in Table 1.

Example 6

Biological Studies Utilizing NiTCP—16 hours

Seven mice having KHJJ mammary carcinomas were injected with the NiTCP solution in the amount of 160 $\mu$g NiTCP/g body weight (36 $\mu$gB/g body weight) in six i.p. injections over 20 hours.

Sixteen hours after the mice were injected with NiTCP, mice were euthanized during the collection of blood while under Halothane anesthesia and right ventricular blood was collected from each mouse for hematological and chemical analysis without pooling the samples. At necropsy, the apparent states of structural integrity, consistency, color, or abnormality, if any, of tissues were observed and tumor, brain and liver tissues were collected from each mouse for boron analysis. Results relating to toxicity and efficacy of NiTCP are set forth in Table 1.

Example 7

Biological Studies Utilizing NiTCP—78 hours

Eight mice having KHJJ mammary carcinomas were injected with the NiTCP solution in the amount of 160 $\mu$g NiTCP/g body weight (36 $\mu$gB/g body weight) in six i.p. injections over 20 hours.

78 hours after the mice were injected with NiTCP, mice were euthanized during the collection of blood while under Halothane anesthesia and right ventricular blood was collected from each mouse for hematological and chemical analysis. At necropsy, the apparent states of structural integrity, consistency, color or abnormality, if any, of tissues were observed and tumor, brain and liver tissues were collected from each mouse for boron analysis without pooling the samples. Results relating to toxicity and efficacy of NiTCP are set forth in Table 1.

About 0.4 ml of each blood sample of Examples 4–7 was collected for chemical analysis conducted in accordance with the methods discussed in Example 3B above. Similarly, about 0.2 ml of each blood sample of Example 4–7 was collected for hematological analyses. Additionally, 50–130 mg each of tumor, brain and liver tissue samples of Examples 4–7 were collected for boron analysis.

The results of the weight, chemical, hematological, and boron analysis of samples obtained from Examples 4 to 7 are illustrated in Table 1 below. Entries show median value followed by range in parentheses. Percent weight difference uses the weight of mice the day the injections were initiated as the reference point.

significant difference occurred 16 hours after injections and by seventy-eight hours after injections this minor, evidently transient, elevation in BUN appears to be subsiding. Neither the transient weight loss nor the transient elevation of BUN was associated with any discerned abnormality of individual mouse activity or interactive behavior in the mouse cage.

The ALP and ALT were somewhat depressed 78 hours after injections and had not been so at earlier time points. However, as is shown in Table 2 below, when these enzyme levels in mice given a higher dose of NiTCP are compared to levels in mice given solvent vehicle only, instead of being compared to levels in mice given BPA, there was no significant difference.

A compound of the present invention, NiTCP, has the ability to deliver twice the amount of boron to tumor than

TABLE 1

| Example (Drug) | 4 (BPA) | 5 (NiTCP) | 6 (NiTCP) | 7 (NiTCP) |
|---|---|---|---|---|
| Period after last injection | 6 hr | 6 hr | 16 hr | 78 hr |
| Dose $\mu$g compound/gbw | 900 | 160 | 160 | 160 |
| Dose $\mu$gB/gbw | 43 | 36 | 36 | 36 |
| No. of mice | 7 | 8 | 7 | 8 |
| Δ weight (%) | 3.3 (0.9–6.5) | −1.4 (−3.3–1.8) | 0.9 (−0.4–7.7) | 2.8 (−1.4–8.8) |
| GLU (mg/dl) | 184 (139–232) | 189 (143–254) | 196 (176–248) | 212 (172–288) |
| BUN (mg/dl) | 19 (13–23) | 30 (15–36)[c] | 28 (2–35)[b] | 22 (19–26)[c] |
| BCR (mg/dl) | 0.5 (0.5–0.5) | 0.5 (0.4–0.6) | 0.4 (0.4–0.6) | 0.5 (0.5–0.6) |
| ALT (u/l) | 28 (21–23) | 33 (21–68) | 27 (23–65) | 22 (16–25)[c] |
| AST (u/l) | 84 (58–165) | 97 (57–226) | 122 (84–136) | 126 (73–197) |
| ALP (u/l) | 61 (39–94) | 51 (36–94) | 51 (42–65) | 27 (18–35)[a] |
| TPR (g/dl) | 4.5 (4.3–4.9) | 5.2 (4.7–5.7) | 4.8 (4.5–5.2) | 4.6 (4.4–5.0) |
| ALB (g/dl) | 2.6 (2.4–2.9) | 3.0 (2.5–3.3) | 2.7 (2.5–3.0) | 2.6 (2.4–3.0) |
| CPK (u/l) | 88 (42–165) | 108 (64–211) | 77 (47–301) | 64 (42–148) |
| Platelets ($10^3$ mm$^3$) | 879 (454–992) | 869 (560–1022) | 562 (421–869) | 659 (547–879) |
| WBC ($10^3$ mm$^3$) | 11.8 (7.5–14.2) | 5.7 (3.6–23-6) | 7.3 (5.8–14.5) | 14.9 (6.1–20.0) |
| Boron Concentration: | | | | |
| Tumor ($\mu$g B/g) | 13.8 (11.3–21.0) | 26.6 (20.3–42.8) | 25.5 (16.2–38.7) | 17.0 (9.2–28.2) |
| Brain ($\mu$g B/g) | 7.2 (3.3–10.6) | 7.2 (3.2–11.1) | 3.8 (2.4–5.0) | 1.7 (0.1–0.2) |
| Blood ($\mu$g B/g) | 4.6 (0.9–9.3) | 55.7 (33.0–74.0) | 13.2 (4.2–30.5) | 0.2 (0.4–5.8) |

[a]–[c]Non-parametric Wilcoxon Two-Sample test shows these values to differ from BPA control sample with the following uncertainties: [a]$P < .001$, [b]$P < .002$, [c]$P < .05$
All tests used a 10% allowable percent difference except CPK and BCR which used 40% allowable percent difference.

The resulting data in Table 1 demonstrate that NiTCP is similar in its toxicity to that of the currently used boron-carrier, BPA. Both toxicities were either undetectable, minimal, or negligible in every respect except that plasma and some tissues (notably the liver) of NiTCP-treated mice were slightly darker than those from normal, solvent-injected mice. Tumor, brain, liver, and other tissues were observed to be normal in appearance at necropsy. In particular, zones of petechial hemorrhage attributed to thrombocytopenia, which is known to be caused by therapeutically relevant doses of other boronated and non-boronated porphyrins known to the art of experimental, so-called "preclinical" BNCT research, were not observed.

Table 1 shows that the weight change in mice given the compound of the present invention (NiTCP) sixteen and seventy-eight hours after the last injection were similar to those in mice given the presently used boron compound BPA. However, some minor, evidently transient, weight loss was noted six hours after the last NiTCP injection.

Table 1 demonstrates that, six and sixteen hours after the last injection, the blood plasma levels of all the tested analytes in mice given NiTCP are the same or similar to those in mice given BPA except BUN. The BUN levels in mice given NiTCP at all three time points were higher than those in mice given BPA in Example 4. However, the most that of BPA at similar boron doses at the 6-hour time point. However, the blood boron concentration from NiTCP is double that of tumor at this time. It is important to note that 78 hours after injection the tumor-to-blood ratio from NiTCP, of approximately 85:1, is theoretically more suitable for BNCT than is the concurrent ratio from BPA. The tumor-to-normal brain ratio from NiTCP is about 7:1 16 hours to 78 hours after injection.

The following examples are presented to demonstrate that, even when a higher dosage of NiTCP was utilized in preclinical BNCT experiments, it displays little if any appreciable toxicity, and was capable of delivering a high concentration of boron to tumor with a low concentration of boron to brain tissue. Although blood boron was unacceptably high at early time points, the boron rapidly cleared from the blood. Therefore, unlike BPA, for which the issue of blood boron is clinically serious and generally considered to be unfavorable in terms of its potential for causing concomitant damage to normal brain tissues during BNCT of a brain tumor, the issue of blood boron for NiTCP is neither unfavorable nor serious, since robust tumor concentrations could be achieved when both normal brain and blood concentrations had fallen to negligible levels with time. Likewise, the serious issue of thrombocytopenia that arises from injection of all other boronated (and same non-boronated at similar doses) porphyrins hitherto known to the art of experimental BNCT was not an issue from injection of NiTCP, a boronated porphyrin of the present invention.

Example 8

Biological Studies Utilizing Control Samples of a Solvent Solution Containing CRM and PrG—17 hours Four mice having KHJJ mammary carcinomas were each given six i.p. injections over 32 hours with a solvent solution containing 9% CRM and 18% PrG. using 0.02 ml/g body weight/injection.

Seventeen hours after the mice were injected with the solvent solution, right ventricular blood was collected from each mouse while under halothane anesthesia for individual hematological and chemical analyses. At necropsy, the appearances of tissues were observed and tumor, brain and liver tissues were collected from each mouse for boron analysis. Results relating to toxicity and efficacy of the control sample are set forth in Table 2.

Example 9

Biological Studies Utilizing Control Samples of a Solvent Solution Containing CRM and PrG—4 days Four mice bearing KHJJ mammary carcinomas were given six i.p. injections over 32 hours with 0.02 ml/g body weight/ injection of a solvent solution containing 9% CRM and 18% PrG.

Four days after the mice are injected with the solvent solution, right ventricular blood is collected from each mouse while under halothane anesthesia for hematological and chemical analysis. At necropsy, the appearances of tissues were observed and tumor, brain and liver tissues were collected from each mouse for boron analysis. Results relating to toxicity and efficacy of the control sample are set forth in Table 2.

Example 10

Biological Studies Utilizing NiTCP—17 hours

Six mice having KHJJ mammary carcinomas were injected with a NiTCP solution in the amount of 244 μg NiTCP/g body weight (54 μg B/g body weight) in six i.p. injections over 32 hours. The NiTCP solution was prepared in accordance with the procedures described in Example 2A except that the percentage of CRM and PrG were increased to 9% and 18%, respectively. Also, the concentration of NiTCP was increased to 2.27 mg NiTCP/ml. The injection volume (0.02 ml/g body weight/injection) was kept identical to that described in Examples 5, 6 and 7.

Seventeen hours after the mice were injected with NiTCP, mice were euthanized during the collection of blood while under halothane anesthesia and right ventricular blood was collected from each mouse for hematological and chemical analysis. At necropsy, the appearances of tissues were observed and tumor, brain and liver tissues were collected from each mouse for boron analysis individually. Results relating to toxicity and boron biodistribution of NiTCP are set forth in Table 2.

Example 11

Biological Studies Utilizing NiTCP—2 days

Six mice having KHJJ mammary carcinomas were injected with the NiTCP solution in the amount of 244 μg NiTCP/g body weight (54 μg B/g body weight) in six i.p. injections over 32 hours. The NiTCP solution was prepared in accordance with the procedures described in Example 10.

Two days after the mice were injected with NiTCP, mice were euthanized during the collection of blood while under halothane anesthesia and right ventricular blood was collected from each mouse for chemical analysis. At necropsy, the appearances of tissues were observed and tumor, brain and liver tissues were collected from each mouse for boron analysis. Results relating to toxicity and efficacy of NiTCP are set forth in Table 2.

Example 12

Biological Studies Utilizing NiTCP—4 days

Six mice having KHJJ mammary carcinomas were injected with the NiTCP solution in the amount of 244 μg NiTCP/g body weight (54 μg B/g body weight) in six i.p. injections over 32 hours. The NiTCP solution was prepared in accordance with the procedures described in Example 10.

Four days after the six mice were injected with NiTCP, mice were euthanized during the collection of blood while under Halothane anesthesia and right ventricular blood was collected from each mouse for hematological and chemical analysis. At necropsy, the appearances of tissues were observed and tumor, brain and liver tissues were collected from each mouse for boron analysis. Results relating to toxicity and efficacy of NiTCP are set forth in Table 2.

The chemical analysis of blood samples and the boron analysis were carried out as described in Example 3 above. The results, for examples 8 to 12, of the chemical analysis of blood samples and boron analysis are set forth in Table 2.

The results of the weight, chemical, hematological, and boron analysis of the samples from Examples 8 to 12 are shown in Table 2 below.

TABLE 2

| Example (Drug) | 8 (Solvent) | 9 (Solvent) | 10 (NiTCP) | 11 (NiTCP) | 12 (NiTCP) |
|---|---|---|---|---|---|
| Period after last injection | 17 hr | 4 d | 17 hr | 2 d | 4 d |
| Dose μg compound/gbw | | | 244 | 244 | 244 |
| Dose μgB/gbw | 0 | 0 | 54 | 54 | 54 |
| No. of mice | 4 | 4 | 6 | 6 | 6 |
| Δ weight (%) | 2.0 (−2.0–3.5) | 6.8.(2.1–8.8) | −2.2 (−4.7–0.9)[b] | 1.6 (−1.8–7.5) | 2.4 (−1.7–10.7) |
| GLU (mg/dl) | 180 (163–231) | 214 (184–220) | 196 (161–285) | 214 (187–272) | 218 (166–257) |
| BUN (mg/dl) | 20 (16–27) | 20 (18–23) | 20 (12–25) | 20 (17–30) | 22 (18–25) |
| BCR (mg/dl) | 0.4 (0.4–0.5) | 0.4 (0.4–0.5) | 0.4 (0.4–0.5) | 0.4 (0.4–0.5) | 0.4 (0.4–0.5) |
| ALT (u/l) | 22 (18–25) | 26 (23–33) | 27 (17–37) | 28 (21–39) | 21 (14–23)[a] |
| AST (u/l) | 142 (96–174) | 260 (154–130) | 55 (53–122)[b] | 117 (76–303) | 168 (95–296) |
| ALP (u/l) | 44 (11–56) | 36 (34–37) | 58 (36–74) | 40 (37–83) | 32 (28–45) |

TABLE 2-continued

| Example (Drug) | 8 (Solvent) | 9 (Solvent) | 10 (NiTCP) | 11 (NiTCP) | 12 (NiTCP) |
|---|---|---|---|---|---|
| TPR (g/dl) | 4.6 (4.1–4.7) | 4.8 (4.7–5.2) | 4.8 (4.1–5.5) | 4.8 (4.4–5.2) | 4.8 (4.5–5.3) |
| ALB (g/dl) | 2.3 (2.1–2.4) | 2.6 (2.6–2.9) | 2.6 (2.0–2.7) | 2.6 (2.4–2.8) | 2.6 (2.3–2.7) |
| CPK (u/l) | 271 (148–581) | 116 (100–175) | 85 (38–770) | 148 (79–190) | 121 (80–159) |
| Platelets ($10^3$ mm$^3$) | 830 (520–891) | 609 (607–761) | 748 (625–900) | 708 (507–794) | 552 (311–711) |
| WBC ($10^3$ mm$^3$) | 6.2 (5.2–9.5) | 15.4 (10.6–18.9) | 10.5 (5.9–14.1) | 14.0 (11.5–39.9) | 10.5 (9.5–19.1) |
| Boron Concentration: | | | | | |
| Tumor ($\mu$g B/g) | 0 | 0 | 52.1 (36.9–82.9) | 68.8 (40.3–179.0) | 41.6 (27.5–158) |
| Brain ($\mu$g B/g) | 0 | 0 | 1.6 (1.3–2.0) | 6.2 (2.3–9.2) | 4.7 (2.7–12.3) |
| Blood ($\mu$g B/g) | 0 | 0 | 91.8 (59.8–123.3) | 19.3 (15.6–41.6) | 0.2 (0.1–0.4) |

[a]–[b]The non-parametric Wilcoxon Two-Sample test shows these values to differ from controls with the following uncertainties:
[a]$P < 0.05$, [b]$P < 0.10$.
All tests used a 10% allowable percent difference except CPK and BCR which used 40%.

The resulting data in Table 2 demonstrate that one of the compounds of the present invention, NiTCP, is non-toxic. In addition, NiTCP has the ability to deliver high concentrations of boron to tumor with low concentrations of boron to other tissues including normal brain tissues and blood after a certain period following injection.

Table 2 shows the toxicological data of mice given NiTCP at a total dose of 244 $\mu$g/g body wt 17 hours, 2 and 4 days after the last injection. These values are compared to those of mice given solvent only 17 hours and 4 days after injection.

There are only slight differences in the results of blood chemical analyses between the NiTCP groups and the solvent-only control groups: A transient reduction in AST levels 17 hours after injection that did not exist 1 day later and depression of ALT 4 days after the last injection of NiTCP compared with the 4-day control group (but not with the 17-hour control group). Weight loss was only observed 17 hours after the last injection of NiTCP.

Boron concentration is high in tumor and low in brain tissue and blood (after a sufficient period of time after injecting) in mice given the compound of the present invention, as shown in Table 2. More specifically, at four days after the last injection, the tumor:brain tissue boron concentration ratio is about 10:1, and the tumor:blood boron concentration ratio is about 250:1. In contrast, the corresponding ratios for BPA at an optimum tumor boron concentration (typically several hours, not days) are between 3.5:1 and 4:1. The much larger ratios achievable by NiTCP with the concomitant larger absolute concentrations of boron in tumor, indicate clearly the promise of NiTCP for development as a unique or adjunct $^{10}$B- carrier in clinical BNCT.

In addition, Table 2 shows that the tumor boron concentrations in mice given NiTCP 4 days after the last injection and 17 hours after the last injection are very similar. Thus, the compound of the present invention has the ability to retain the therapeutic amounts of boron in the tumor for several days.

Example 13

Toxicity Testing of NiTCP, MnTCP and CuTCP in Mice—4 days

Compounds prepared as in Example 1B and 1C were formulated with 6% Cremophor EL [CRM] and 12% propylene glycol [PrG] in saline. Total doses of MnTCP and CuTCP of 174 and 223 $\mu$g/g body weight, respectively, were administered to normal BALB/c mice. Each mouse was given 6 intraperitoneal [ip] injections over a period of 32 hours. Mice were euthanized 4 days after the last injection and chemical, enzymatic and hematological analyses of their blood were compared to those of similar mice given NiTCP at a dose of 252 $\mu$g/g body weight. The results are shown in Table 3.

TABLE 3

Hematologic, enzymatic, and chemical analyses of blood from mice given the designated metalloporphyrin 4 days after the last of 6 ip injections.

| | NiTCP 252 | | | MnTCP 174 | | | CuTCP 223 | | |
|---|---|---|---|---|---|---|---|---|---|
| Group Dose ($\mu$g/gbw) | 1 | 2 | 3 | 1 | 2 | 3 | 1 | 2 | 3 |
| Δ % wt | 4.5 | 5.2 | 2.6 | 1.2 | 3.8 | 2.5 | -3.2 | 2.0 | -0.4 |
| GLU (mg/dl) | 187 | 262 | 234 | 222 | 179 | 180 | 169 | 247 | — |
| BUN (mg/dl) | 27 | 27 | 21 | 20 | 22 | 30 | 20 | 19 | 22 |
| BCR (mg/dl) | 0.5 | 0.5 | 0.5 | 0.6 | 0.5 | 0.6 | 0.5 | 0.5 | — |
| ALT (u/l) | 19 | 14 | 13 | 16 | 15 | 16 | 17 | 15 | 18 |
| AT (u/l) | 51 | 40 | 41 | 39 | 43 | 43 | 47 | 44 | 49 |
| ALP (u/l) | 69 | 67 | 79 | 73 | 73 | 68 | 65 | 66 | 82 |
| CPK | 30 | 33 | 30 | 35 | 25 | 40 | 46 | 41 | 38 |
| ALB | 3.0 | 3.0 | 2.8 | 2.9 | 3.1 | 2.8 | 3.1 | 3.1 | — |
| TPR (g/dl) | 5.3 | 5.4 | 5.3 | 5.4 | 5.4 | 5.4 | 5.4 | 5.5 | — |
| platelets | 723 | 757 | 559 | 639 | 575 | 609 | 740 | 664 | 630 |

Table 3 shows that there is little if any difference in toxicity between mice given MnTCP or CuTCP, to those of mice given NiTCP, which has been shown to be nontoxic. Moreover, the level of platelets did not decrease (i.e. no thrombocytopenia was observed) with any of the porphyrins, which could otherwise be a serious issue for patients being treated with BNCT for glioblastoma multiforme. This lack of thrombocytopenia upon administering these compounds represents a significant advantage particular to the compounds of the present invention.

Example 14

Testing of CuTCP in Rats Bearing Subcutaneous 9L Gliosarcomas for Boron Concentration Male Fischer 344 rats each bearing 4 subcutaneous 9L gliosarcomas were given 210–219 mg CuTCP/kg body wt by 48-h iv infusion. Tumor and blood were sampled at 0, 1, 2, and 3 days after the end of infusion for boron analyses and blood for toxicity. Rats were euthanized on day 3 and other organs were analyzed for boron uptake.

Figure 2:
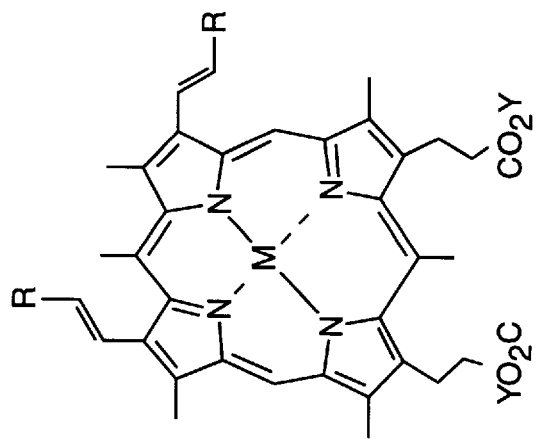
FIG. 2 shows the chemical formulas for derivatives of tetraphenylporphyrin and derivatives of heme, a natural porphyrin found in hemoglobin or myoglobin.
Figure 2:
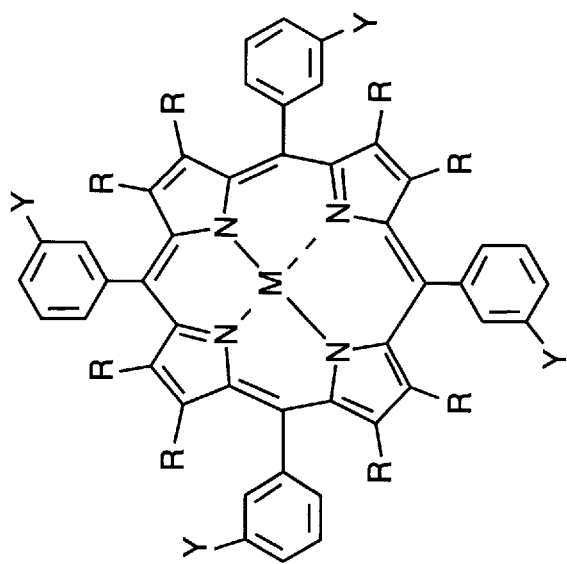

The infused rats showed no abnormalities either in their physical appearance or behavior. Hematologic, chemical and enzymatic assays showed no deviations from rats infused with solvent only. Tumor boron concentrations were high in rats given CuTCP by 48-h infusion as compared to mice given an equal whole body dose of NiTCP via serial i.p. injections. Boron concentrations of 54–68 $\mu$g B/g were found in tumor tissue immediately after the end of infusion and stayed at 38–69 $\mu$g B/g after 2d as shown in FIG. 2.

Significantly, this is the first demonstration of a boronated porphyrin given to a rat bearing a subcutaneously implanted glioma that results in therapeutic amounts of boron in tumor and very rapid blood clearance with no toxicity, in particular, with no thrombocytopenia.

The rapid and almost total clearance of boron in blood within 2 days has not been observed with other porphyrins. It appears more rapid than in mice given NiTCP at a total dose of 244 $\mu$g/g body wt, where it took 4 days before the average blood boron concentration falls below 1 ppm. At necropsy, the brain was separated into cerebellum and cerebrum, and each contained the same average concentration of boron, 1–2 $\mu$g B/g.

Several similar experiments were carried out at various infusion periods between 2 hours and 48 hours. It appears that the porphyrins need a minimum period of time at high blood concentration in order to localize in tumor tissue in high concentration. Another important factor in the pharmacokinetics of blood boron was the infusion volume. If it was too great when normalized to rat weight, the boron in blood remains high for a longer period of time. A total dose of 215 mg/kg body weight in 0.064 mL infusion volume/g body weight, 48 hours after the end of infusion, appears optimal since medians of 55 and 6$\mu$g B/g were found in tumor and blood, respectively. In the cerebellum and cerebrum, there were 1.5 and 2.5 $\mu$g B/g, respectively.

Example 15

Testing of CuTCP-H in Rats Bearing Subcutaneous 9L Gliosarcomas for Biodistribution and Toxicity CuTCP-H (146–152 mg/kg body weight) was given to four Fischer 344 rats each bearing four subcutaneous 9L gliosarcomas. A solution of 3.34 mg CuTCP-H/mL, in 9% CRM and 18% PrG, was given to rats by 48-hour i.v. infusion in a total volume of 9.6 mL.

The physical appearance and behavior of porphyrin-infused rats were no different from untreated rats. Some weight loss occurred, but this is commonly observed when rats are restrained with a tether for prolonged periods of time. All rats started to gain weight after the tethers were removed.

The tumor boron concentrations were similar to that for CuTCP in rats. The optimal time for BNCT appears to be 48 hours after the end of infusion when the median tumor value is 32 $\mu$g B/g and the median blood value is 2 $\mu$g B/g giving a 16:1 tumor:blood ratio as shown in Table 4. As with CuTCP, the dose can be increased to greater than 200 mg/kg, so that tumor boron concentrations may be greater than 40 $\mu$g B/g.

TABLE 4

Boron concentrations in various tissues after Fisher rats bearing 9L gliosarcomas were infused with 149 mg CuTCP-H/kg body weight over 48 hours.

| Time after infusion | 0 days | 1 day | 2 days | 5 days |
|---|---|---|---|---|
| Tumor | 45 (23–51) | 46 (35–52) | 32 (27–41) | 31 (23–55) |
| Blood | 183 (160–205) | 62 (56–65) | 2.1 (1.1–8.1) | 0.6 (0.3–0.7) |
| Liver | — | — | — | 345 (336–408) |
| Cerebrum | — | — | — | 4.9 (2.2–6.9) |
| Cerebellum | — | — | — | 2.8 (2.1–6.2) |

Example 16

Comparison of Biodistribution and Toxicity Properties in Mice of Various Boronated Porphyrins The following examples describe a comparison of boronated porphyrins of the present invention with boronated natural or heme derivatives. Both lipophilic and water soluble forms of these compounds are examined. This comparison demonstrates the advantages of the boronated porphyrins of the present invention over the prior art compounds.

Toxicity and biodistribution tests in mice of seven different porphyrins, four containing nickel, including NiTCP, one copper, one zinc and one free base porphyrin were conducted. The porphyrin structures can be classified as either derivatives of tetraphenylporphyrin [TPP], or as derivatives of heme, a natural porphyrin found in many proteins such as hemoglobin and myoglobin. Within each of these two classifications, a further division is made to distinguish water-solubility. FIG. 2 shows that porphyrins 1–4 are TPP derivatives and 5–7 are heme derivatives and only those with nido carborane cages ($B_9H_{10}^-$ moiety) are charged and are therefore water-soluble (porphyrins 3 and 7).

NiTCP-H, 2, is an analog of NiTCP and CuTCP because they have the same carboranylphenyl substituents at their meso positions. However, the methyl acetate groups are replaced by hydrogens at the pyrrolic positions. Porphyrin 2 without nickel was first synthesized as a precursor to the free-base derivative of NiNTCP-H, 3 in which the carborane cages have been degraded to the nido form as described in Oenbrink, et al., 1988. The synthesis of porphyrins 2 and 3 is described in Miura et al., 1990 which is incorporated herein by reference as if set forth in full. NiDPE, 5, and its zinc analog, 6, are natural porphyrin derivatives that contain carborane cages at the 3 and 8 positions via vinyl linkages. Porphyrin 6 is an intermediate in the synthesis of water-soluble 3,8-divinyl-nido-carboranyldeuteroporphyrin (VCDP), 7, which has been studied extensively in the murine KHJJ mammary tumor model (Miura et al., 1992) and is studied here in the murine EMT-6 mammary tumor. The toxicities and biodistribution of CuTCP, 4, and BPA were also compared. There are available isotopes of copper that are imageable by SPECT, which would be of great value for BNCT treatment planning.

16A. Materials and Methods a. Synthesis of Compounds

NiTCP and CuTCP were synthesized as described in Examples 1A and 1B herein. ZnDPE and VCDP were synthesized as described in Miura et al., 1990. The metal-free (free base) derivatives of porphyrins 2, 3 and 5 as shown in FIG. 2 were synthesized as described in Miura et al., 1990 and nickel was inserted as described in Example 1A. Spectral characterization data is set forth below as follows:

Porphyrin 2, NiTCP-H: NMR (CDCl$_3$): 8.73 (s, 8H, pyrrole H), 7.19–7.75 (m, 16H, ArH), 4.55 (s, 8H, OCH$_2$), 4.12 (s, 4H, carborane CH), 1.5–3.3 (br. m, 40H, BH); UV-vis (CH$_2$Cl$_2$)λmax (nm): 413, 555.

Porphyrin 3, NiNTCP-H: NMR (d6-acetone): 8.92 (s, 8H, pyrrole H), 7.67–7.72 (m, 12H, ArH), 7.37–7.40 (m, 4H, ArH), AB quartet, 4.39 (d, 4H, OCH$_2$), 4.08 (d, 4H, OCH$_2$), 2.14 (s, 4H, carborane CH), 0.7–2.4 (br. m, 36H, BH); UV-vis (CH$_2$Cl$_2$)λmax (nm): 414, 532, 564.

Lipophilic porphyrins 1, 2, 4, 5, and 6 were injected as emulsions in either 3% or 9% CRM and either 6% or 18% PRG with saline as previously described in Example 2 above. Water soluble porphyrins 3 and 7 were dissolved in saline. BPA was solubilized as a fructose complex.

b. Preparation of Animals

Female BALB/c mice (from Taconic Farms, Germantown, N.Y.) (20–25 g) were implanted with either KHJJ or EMT-6 tumors according to the procedure described in Example 3A above.

Under deep halothane anesthesia leading to euthanasia, right ventricular blood was collected in Microtainer (Becton-Dickinson, Rutherford, N.J.) tubes containing EDTA for hematological analyses and boron assays of whole blood and in Microtainer™ tubes containing lithium heparin for chemical analyses and enzyme assays of blood plasma. Tumor, brain, fat, muscle, and liver tissues were sampled at necropsy for boron analyses.

c. Drug Administration and Euthanasia Schedule

Hematological, chemical, enzymatic and boron concentration tests were conducted on mice bearing KHJJ and EMT-6 tumors in four different experiments as summarized below and set forth in Table 5 also below.

In Experiment I, NiTCP (183 μg/gbw) and lipophilic, heme derivative ZnDPE (118 μg/gbw) were compared in mice bearing KHJJ mammary tumors. The porphyrins were given as 3% CRM and 6% PrG emulsions in 3 ip injections given over 8 hrs. Animals were euthanized 15 hr, 39 hr, and 90 hr after the last injection. The hematological, chemical and enzymatic test results are shown in Table 7.

In Experiment II, NiDPE (78 μg/gbw), NiNTCP-H (93/μg/gbw) and VCDP (245 μg/gbw) were compared in mice bearing EMT-6 mammary tumors which were euthanized 90 hr after the last injection.

Results of hematological, chemical and enzymatic tests of blood from mice bearing EMT-6 mammary tumors given NiDPE (78 μg/gbw )and NiNTCP-H (93 μg/gbw) in 6 ip injections given over 32 hours are set forth in Table 6 below. Results of the same tests for VCDP are set forth in Miura et al., 1992 incorporated herein by reference as if set forth in full.

In Experiment III, NiTCP and NiTCP-H were compared in mice bearing EMT-6 mammary tumors. Each porphyrin was administered via 6 i.p. injections over a period of 32 hours and the mice were euthanized 39 hours and 90 hours after the last injection. The results of boron concentration in various tissues are given in Table 8.

In Experiment IV, samples of BPA (836 μg/gbw), CuTCP (160 μg/gbw) and a combination of both were tested in mice with EMT-6 tumors. BPA was given in a single i.p. injection and mice were euthanized 6 hours later. CuTCP was given in 5 i.p. injections over 28 hours and mice were euthanized 90 hrs after the last injection. The group receiving both CuTCP and BPA were injected with CuTCP five times over 28 hours as was the CuTCP-only group and then with a single i.p. injection of BPA 6 hours prior to euthanasia which was 90 hours after the last injection of CuTCP. The results of boron concentration in various tissues can be seen in Table 10.

Each experiment described above is summarized in Table 5.

TABLE 5

The porphyrins used in each experiment, their dose, and other experimental details.

| Expt | Porphyrin | Dose (μg/gbw) | Tumor | % CRM | # ip injections | Injection period | Clearance period |
|---|---|---|---|---|---|---|---|
| I | NiTCP | 183 | KHJJ | 3 | 3 | 8 hr | 15 hr, 39 hr, 90 hr |
| I | ZnDPE | 118 | KHJJ | 3 | 3 | 8 hr | 15 hr, 39 hr, 90 hr |
| II | NiDPE | 78 | EMT-6 | 9 | 6 | 32 hr | 90 hr |
| II | NiNTCP-H | 93 | EMT-6 | 0 | 6 | 32 hr | 90 hr |
| II | VCDP | 245 | EMT-6 | 0 | 12 | 80 hr | 90 hr |
| III | NiTCP | 183 | EMT-6 | 9 | 6 | 32 hr | 39 hr, 90 hr |
| III | NiTCP-H | 191 | EMT-6 | 9 | 5–6 | 32 hr | 39 hr, 90 hr |
| IV | BPA | 837 | EMT-6 | 0 | 1 | — | 6 hr |
| IV | CuTCP | 160 | EMT-6 | 9 | 5 | 28 hr | 90 hr |
| IV | BPA + CuTCP | 837 + 160 | EMT-6 | 0, 9 | 6 | 28 hr | 6 hr, 90 hr |

Hematological, chemical and enzymatic tests were carried out as described in Example 3 above. Nonparametric statistical analyses were carried out using the Wilcoxon Two-Sample Test in accordance with procedures described in Slatkin, D.N., 1995. Boron analyses were conducted in accordance with the procedure described in Example 3 above. Fat and liver tissues were assayed for $^{10}$B by prompt-gamma spectroscopy as described in Fairchild, et al., 1986. These measurements were multiplied by 5.0 to give total boron concentrations due to the use of boron of natural isotope abundance in the syntheses of all boronated porphyrins reported.

16B. Toxicity Results

Mice given each porphyrin were compared for hematological, chemical, and enzymatic properties of their blood to either a solvent-only or a NiTCP group. NiTCP causes no mortality (n>80) nor any substantial toxicity at total doses of up to 272 µg/gbw (Miura, et al., 1996). There were no differences in any of the toxicity parameters between mice given 191 µg NiTCP-H/gbw from those of mice given 183 µg NiTCP/gbw at both 32 hr and 90 hr after the last injection of 6 i.p. injections Experiment III.

When mice were given a relatively low dose of the water-soluble, NiNTCP-H (93 µg/gbw) in 6 i.p. injections as shown in toxicity results for Experiment II, there were no visible signs of toxicity until 39 hrs after the last injection. At this time, mice were either found dead or moribund, in which case they were euthanized immediately as shown in Table 6. During necropsy of the moribund animals, the abdominal cavity contained large amounts of bloody fluid and there was brown perianal staining of fur, indicative of diarrhea. Five of the seven mice in this group had lost weight at the 39 hr timepoint as shown in Table 6 below. The weight gains in the remaining two mice were less than that of any control mouse.

Lipophilic natural porphyrin derivatives NiDPE and ZnDPE were tested at the relatively low doses of 78 and 118 µg/gbw, as shown in Tables 6 and 7, respectively. ZnDPE was given at three times the rate that NiDPE was given, 118 µg/gbw in 3 ip injections over 8 hr as compared with 78 µg/gbw in 6 ip injections over 32 hr. At 15 hour, mice given ZnDPE did not appear as healthy as did the controls (lethargy and piloerection) and their liver and kidney enzymes were significantly altered as shown in Table 7. Weight loss was greater in mice given ZnDPE as compared with controls and weight remained subnormal 4 days after the last injection. The effect on kidney and liver enzymes subsided with time. Of 14 mice given ZnDPE, one mouse was found dead on day 2. At this time surviving mice showed that only GLU, ALT, and ALP were altered and by 4 days, only ALT was abnormal. Although NiDPE was given at a lower total dose at a slower dose rate, it apparently caused 2 deaths in a group of 5 mice so treated. The three survivors displayed a healthy appearance and their blood analytes were normal 4 days after injections, except CPK was slightly low for NiDPE as set forth in Table 6.

TABLE 6

Experiment II: Hematological, chemical, and enzymatic tests of blood from mice bearing EMT-6 tumors given either solvent only NiTCP, NiDPE, NiNTCP-H taken 90 hrs after the last injection.

|  | Solvent only | NiTCP | NiDPE | NiNTCP-H |
|---|---|---|---|---|
| Dose (µg/gbw) |  | 183 | 78 | 93 |
| Number of mice | 7 | 7 | 5 | 7 |
| No. Dead or moribund mice | 1 | 0 | 2 | 7 |
| % Δw (2 d) | 6.1 (3.6–8.4) | 5.3 (2.5–6.4) | 1.3 (−1.3–4.6)$^2$ | −2.0 (−4.7–1.2)$^1$ |
| GLU | 222 (169–246) | 190 (144–254) | 212 (194–259) | — |
| BUN | 28 (16–32) | 29 (28–32) | 31 (30–33) | — |
| BCR | 0.6 (0.6–0.7) | 0.7 (0.6–0.9) | 0.7 (0.6–0.8) | — |
| ALT | 18 (15–19) | 19 (16–23) | 17 (13–29) | — |
| AST | 59 (53–65) | 70 (58–118) | 78 (54–82) | — |
| ALP | 30 (24–35) | 31 (25–36) | 31 (23–39) | — |
| CPK | 109 (57–159) | 74 (30–390) | 35 (31–74)$^3$ | — |
| PLT | 1178 (1080–1280) | 1082 (894–1166) | 1090 (1023–1167) | — |

Values are median and the range is shown in parentheses.
[1-4]Wilcoxon 2-Sample Test shows these values to differ from solvent-only controls with the following uncertainties: $^1$p < 0.001, $^2$p < 0.02, $^3$p < 0.10. All tests used a 10% allowable percent difference (Slatkin, 1995) except % Δw, which used 1% and CPK and BCR, which used 40%.

TABLE 7

Experiment I: Hematological, chemical, and enzymatic tests at various timepoints of blood from mice bearing KHJJ tumors given either 118 µg ZnDPE/gbw or 183 µg NiTCP/gbw in 3 ip injections over 8 hr.

|  | 15 hr | 39 hr | 90 hr | 15 hr | 39 hr | 90 hr |
|---|---|---|---|---|---|---|
| Drug | ZnDPE | ZnDPE | ZnDPE | NiTCP | NiTCP | NiTCP |
| % Δw | −6.1 (−0.5–−9.3)$^1$ | −11.3 (−9.0–−12.9)$^4$ | −9.3 (−12.4–−6.2)$^4$ | 0.5 (−3.2–4.1) | 3.9 (3.0–9.2) | 7.8 (5.9–12.1) |
| n | 5 | 4 | 3 | 5 | 5 | 4 |
| GLU | 110 (61–138)$^3$ | 144 (118–168)$^4$ | 146 (112–180) | 199 (183–262) | 210 (183–260) | 218 (172–242) |
| BUN | 77 (28–101)$^2$ | 76 (36–160) | 52 (33–58) | 32 (27–41) | 35 (32–43) | 24 (14–34) |
| BCR | 1.0 (0.5–1.5)$^3$ | 0.6 (0.4–2.1) | 0.6 (0.5–0.6) | 0.5 (0.4–0.5) | 0.4 (0.3–0.4) | 0.4 (0.4–0.4) |
| ALT | 100 (45–287)$^2$ | 116 (78–139) | 44 (34–45) | 28 (21–32) | 32 (27–153) | 27 (26–33) |
| AST | 345 (183–622)$^2$ | 156 (135–191) | 98 (79–155) | 81 (60–146) | 108 (76–442) | 138 (46–285) |
| ALP | 61 (46–62$^5$ | 41 (34–54)$^3$ | 57 (51–59) | 80 (56–86) | 71 (57–88) | 40 (37–80) |
| CPK | 246 (166–448) | 108 (81–124) | 253 (208–502) | 66 (41–289) | 167 (91–227) | 69 (52–94) |

TABLE 7-continued

Experiment I: Hematological, chemical, and enzymatic tests at various timepoints of blood from mice bearing KHJJ tumors given either 118 μg ZnDPE/gbw or 183 μg NiTCP/gbw in 3 ip injections over 8 hr.

|     | 15 hr | 39 hr | 90 hr | 15 hr | 39 hr | 90 hr |
| --- | --- | --- | --- | --- | --- | --- |
| PLT | 857 (891–1162) | 940 (744–1012) | 943 (870–1068) | 733 (579–956) | 826 (790–927) | 790 (553–839) |

Values are median and, in parentheses, range.
[1-4]Wilcoxon 2-Sample Test shows these values to differ from NiTCP controls with the following uncertainties: [1]p < 0.001, [2]p < 0.01, [3]p < 0.02, [4]p < 0.05, [5]p < 0.10.
All tests used a 10% allowable percent difference (Slatkin, 1995), except % Δw, which used 1% and CPK and BCR, which used 40%.

16C. Boron Biodistributions

The boron concentrations in various tissues of mice given the different porphyrins are shown in Tables 8, 9 and 10.

In the EMT-6 tumor, there is much greater uptake of NiTCP-H than of NiTCP as set forth in Table 8. The tumors of mice given 191 μg NiTCP-H/gbw showed a median of 109 μg B/g compared with that in mice given 183 μg NiTCP/gbw which showed a median of only 49 μg B/g. Although the dose of NiNTCP-H was relatively low (93 μg/gbw), the tumor uptake was substantial, showing a median of 38 μgB/g as shown in Table 8.

TABLE 8

Experiment III: Boron concentrations in various tissues (μg B/g) from mice bearing EMT-6 tumors 39 hr and 90 hr after the last of 6 ip injections given either NiTCP, NiTCP-H, or NiNTCP-H.

|  | NiTCP | NiTCP | NiTCP-H | NiTCP-H | NiNTCP-H |
| --- | --- | --- | --- | --- | --- |
| Dose (μg drug/gbw) | 183 | 183 | 191 | 191 | 93 |
| Dose (μg B/gbw) | 41 | 41 | 61 | 61 | 27 |
| Period after injections | 39 hr | 90 hr | 39 hr | 90 hr | 39 hr |
| n | 7 | 17 | 7 | 5 | 7 |
| Tumor | 40 (26–73) | 49 (32–82) | 122 (80–155) | 109 (93–152) | 38 (31–51) |
| Blood | 2.8 (0.8–11.4) | 0.3 (0.1–0.3) | 26 (8–56) | 0.2 (0.1–0.3) | — |
| Brain | 1.6 (1.0–2.5) | 4.2 (1.3–6.0) | 2.0 (0.8–3.9) | 2.2 (0.8–3.4) | 2.0 (0–3.2) |
| Liver | 201 (162–251) | 226 (176–284) | 392 (336–509) | 542 (384–610) | 128 (109–142) |

Table 9 below shows that NiDPE, a lipophilic natural porphyrin derivative has poor tumor localizing properties. Dose escalation was not carried out due to its significant toxicity.

TABLE 9

Experiment II: Boron concentration in various tissues (μB/g) from mice bearing EMT-6 tumors 90 hrs after the last injection of 6 ip injections of NiDPE or the last of 12 ip injections of VCDP.

|  | NiDPE | VCDP |
| --- | --- | --- |
| Dose (μg porphyrin/gbw) | 78 | 245 |
| Dose (μg B/gbw) | 20 | 49 |
| Number of mice | 6 | 6 |
| No. injections | 6 | 12 |
| Tumor | 12 (4.2–12.5) | 53 (30–106) |
| Blood | 0.5 (0.4–0.6) | 7 (4.3–13) |
| Brain | 0.8 (0.6–4.0) | 8.1 (4.9–16.2) |
| Liver | 90 (72–97) | 77 (70–97 |

When the central nickel ion is replaced by copper, another divalent transition metal cation, there appears to be little difference in boron biodistribution as shown in Table 10. When the values for CuTCP are normalized with those for NiTCP, which was given at 14% higher dose, the tissue boron values are similar. To explore the possibility of using boronated porphyrins as an adjunct to BPA for BNCT, the two compounds were given together for observation of any antagonistic or synergistic effect. The results are also shown in Table 10.

TABLE 10

Experiment IV: Boron concentrations in various tissues (μg B/g) from mice bearing EMT-6 tumors 90 hrs after the last injection of 5 ip injections of either CuTCP, CuTCP + BPA, or BPA alone. BPA was given in all cases as 1 ip injection 6 hr before euthanasia.

| Drug | CuTCP | CuTCP with BPA | BPA |
| --- | --- | --- | --- |
| Dose (μg drug/gbw) | 160 | 160 + 837 | 837 |
| Dose (μg B/gbw) | 36 | 36 + 40 | 40 |
| Number of mice | 7 | 8 | 7 |
| Tumor | 45 (34–74) | 58 (36–128) | 5.4 (3.5–23) |
| Blood | 0.3 (0.3–0.5) | 1.5 (0.8–1.8) | 2.0 (1.2–3.6) |
| Brain | 4.2 (0.3–9.5) | 5.5 (1.9–10.4) | 8.1 (5.9–9.6) |
| Liver | 270 (215–308) | 258 (236–320) | 2.1 (0.1–3.1) |
| Muscle | 8.8 (4.0–25) | 7.1 (4.9–9.6) | 3.8 (2.1–7.9) |
| Fat | 44 (31–77) | 39 (28–54) | 0.4 (0–1.8) |

Table 10 shows that the tumor boron uptake of BPA alone in the EMT-6 tumor was low (5.4 μg B/g median). The tissue boron values for CuTCP alone and with BPA show that there is most likely not an antagonistic effect, but there could be a small synergistic accumulation of boron, but either the CuTCP values alone or the BPA values alone are so low it is difficult to determine whether there is, indeed, an additive effect.

Figure 3:
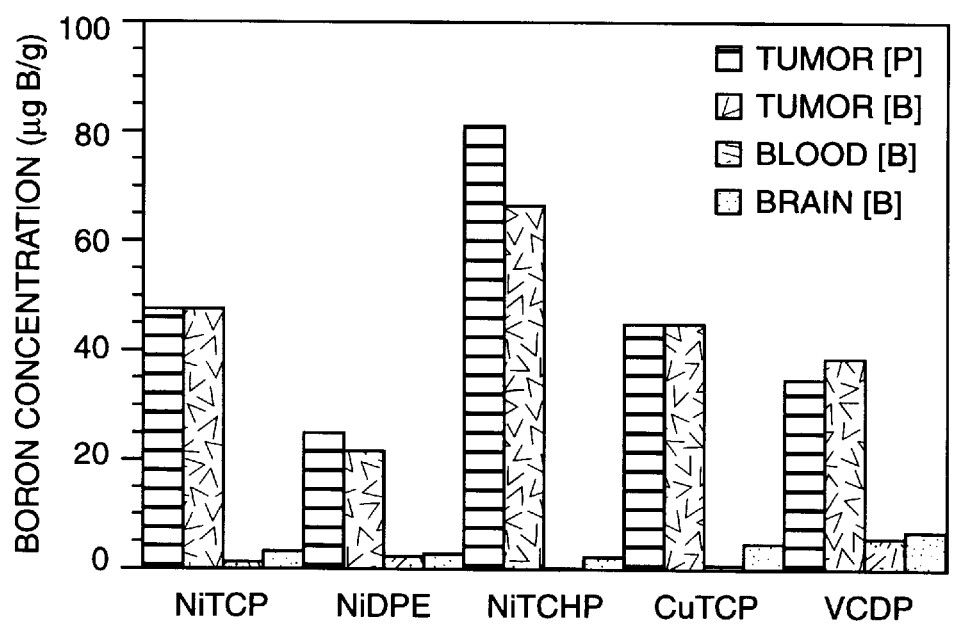
FIG. 3 illustrates normalized boron concentration of BALB/c mice bearing EMT-6 tumors given for NiTCP, NiDPE, NiTCPH, CuTCP or VCDP arithmetically normalized to a constant whole-body dose of porphyrin and boron.

Since the porphyrins were not given at the same dose, the boron concentrations in tumor, blood, and brain were arithmetically normalized to a total dose of 160 μg porphyrin/gbw for comparison in FIG. 3. Since each porphyrin has a different percentage of boron per unit mass, tumor boron concentrations were also arithmetically normalized to a total dose of 36.5 μg B/gbw, also shown in FIG. 3.

At either a constant porphyrin dose, or constant boron dose, the greatest uptake in tumor occurred with NiTCP-H, which was then followed by NiNTCP-H, which was then followed by both NiTCP and CuTCP, which were closely followed by VCDP. The blood boron concentrations were all negligible as were those for brain, which were less than 4 ppm and 12 ppm, respectively.

Unlike most pharmaceutical drugs, the desired function for a BNCT agent is to accumulate in tumor preferentially to other surrounding tissues within the irradiation volume while eliciting little or no toxicity. For brain tumors, high tumor boron sufficient for therapy must be accompanied by low blood and brain boron.

The EMT-6 tumor appears to take up NiTCP, NiTCP-H and VCDP to a greater extent than the KHJJ tumor, even though they are both murine mammary carcinomas. At 90 hrs there was more boron (49 μg B/g median) in the EMT-6 tumors from mice given only 183 μg NiTCP/gbw than there was in the KHJJ tumor (40 μg B/g median) in mice given a 33% larger dose, 244 μg NiTCP/gbw as shown in Table 8 and as discussed in Miura., et al., 1996 incorporated herein by reference as if set forth in full. The EMT-6 was a slower-growing tumor and at 17±2 days after tumor initiation, it was typically less than one-half the size of a KHJJ tumor. Zones of necrosis deep in a large KHJJ tumor did not accumulate boron, so that boron concentrations in viable tumor tissue were actually greater than those listed here. While the tumor uptake was similar for NiTCP and NiTCP-H in the KHJJ tumor, the uptake for NiTCP-H was double that of NiTCP in the EMT-6 tumor as illustrated in Table 8.

The experimental data of Example 16 demonstrates that NiTCP was substantially less toxic, in particular, the absence of thrombocytopenia than VCDP or any other porphyrin reported that has been given to rodents at doses high enough for potential BNCT. Since NiTCP was also the first boronated porphyrin to be delivered in a CRM/PRG emulsion, it was postulated that perhaps the water-insolubility, requiring the use of an emulsifying vehicle might be related to the low toxicity. To test this hypothesis, lipophilic NiDPE and ZnDPE were compared with NiTCP for any similarities in their toxicities elicited in mice as set forth in Table 7. The toxicities of NiTCP were compared with those of its water-soluble analogue, NiNTCP-H which has a structure identical to its lipophilic counterpart except that the carborane cages are degraded to the ionized nido form (Table 6).

From Table 7, it is clear that ZnDPE was more toxic than NiTCP. The lipophilicity of ZnDPE did not alleviate the toxic properties of what has been observed previously with boronated heme derivatives. VCDP exerts toxic effects when mice are given doses greater than 210 μg VCDP/gbw (Miura, et al., 1992). Most notable of these are weight loss, thrombocytopenia, and alterations of some enzymes of hepatic origin. Most of these changes, if not all, had subsided by 90 hrs. ZnDPE, which was given at 118 μg/gbw, also caused weight loss and showed many altered liver and kidney enzyme levels in addition to weight loss (Table 6). For VCDP, the amount of toxicity was more dependent on the rate at which it was given than on the total dose. Only 22 μg VCDP/gbw could be given per injection to keep mortality below 10%. ZnDPE was given at a faster dose rate of 39 μg/gbw per injection and only 1 out of 14 mice died (7% mortality vs. 80% predicted mortality from VCDP), indicating that mice are more tolerant of a faster dose rate of ZnDPE than VCDP. When mice were given a comparable total dose of 130 μg VCDP/gbw over 32 hr, 90 hrs after the last injection, there were no differences from control groups given a bicarbonate solution, although CPK was slightly depressed. (Miura et al., 1992)

Tissue boron biodistributions of VCDP and NiDPE at normalized porphyrin doses are shown in FIG. 3. There was greater tumor uptake of VCDP than of NiDPE (38 vs 25). However, the dose administration period was longer for VCDP, which might promote boron uptake. At those normalized doses, NiDPE delivered less boron to brain and blood, such that the tumor:blood and tumor:brain ratios were greater than those for VCDP. Overall, while VCDP appears similar to ZnDPE and NiDPE in both toxicity and biodistribution, therapeutic amounts of boron were delivered to tumor at high tumor:blood and tumor:brain ratios with VCDP, although at a cost of some toxicity and this has not yet been achieved with NiDPE or ZnDPE, which appear to exhibit the same toxicities.

The toxicities of NiTCP-H and NiNTCP-H were not comparable. The water-soluble NiNTCP-H was vastly more toxic, caused death invariably at half the dose of its lipophilic analogue NiTCP-H, which showed very little toxicity and delivers potentially therapeutic amounts of boron to tumor tissue. Furthermore, the tumor:blood and tumor:brain ratios from NiTCP-H were as favorable or more so than any compound reported to date, to our knowledge.

It has been shown that BPA given as the fructose complex had tumor boron concentrations of ≈14 μg B/g 6 hr postinjection in BALB/c mice bearing KHJJ tumors as set forth in Table 1. Those values are similar to those in which BPA was given as a slurry intragastrically (Coderre et al., 1990). Brain boron was relatively high, with a median of 8 μg B/g and blood was low at 2 μg B/g. It appears that the tumor uptake of BPA, although very high in rat 9L gliosarcomas and murine Harding-Passey melanomas, is considerably lower in these murine mammary carcinomas, particularly in the EMT-6 as illustrated in Table 10.

Although NiTCP-H delivered double the amount of boron to the EMT-6 tumor as did NiTCP in mice, CuTCP-H or NiTCP-H delivered similar amounts of boron to the 9L gliosarcoma in rats or the KHJJ mammary carcinoma in mice as did CuTCP or NiTCP, if boron concentrations were normalized to a constant porphyrin dose. These data, in addition to that for BPA in mammary carcinomas, demonstrate that tumor boron delivery can be dependent on the particular tumor type. However, there appears to be a correlation in biodistribution properties between the KHJJ mammary carcinoma and the 9L gliosarcoma with this particular class of porphyrins.

Table 11 shows the overall ranking of the various porphyrins in their potential ability to deliver high boron concentrations to tumor and their relative toxicities at those doses for clinical BNCT. The higher the numerical value, the better the performance of that porphyrin for that property. FIG. 3 and Table 11 show that, of the porphyrins studied, the TPP's deliver greater amounts of boron to tumor than the heme derivatives even at a constant boron dose. Although VCDP was able to deliver therapeutic amounts of boron to tumor, such side effects such as thrombocytopenia, which was induced within 3 hours after injections, weight loss, and the altered hepatic enzymes were serious enough to rank VCDP considerably behind the TCP's and the TCP-H's (Miura et al., 1992). In addition, the 80-hour drug administration period and the 90-hour blood clearance period are of great inconvenience. Moreover, this 4-day difference between the VCDP and the TCP (or TCP-H) dose and clearance schedules would translate into a 4-day greater delay between initiation of drug administration and neutron irradiation which would allow greater tumor growth to occur.

TABLE 11

Overall ranking of the anticipated quality of boronated porphyrins for BNCT guided by biodistribution and toxicity tests in mice. An asterisk indicates inadequate data.

|  | NiTCP | CuTCP | NiTCPH | NiNTCPH | NiDPE | ZnDPE | VCDP |
|---|---|---|---|---|---|---|---|
| Porphyrin type | TPP | TPP | TPP | TPP | Heme | Heme | Heme |
| Lipophilicity | 2 | 2 | 2 | 0 | 2 | 2 | 0 |
| Tumor uptake (normalized) | 3 | 3 | 4 | 3 | 2 | 2 | 3 |
| Tumor:Blood | 3 | 3 | 4 | * | 2 | * | 2 |
| Drug tolerance/ deliverable boron | 4 | 4 | 4 | 0 | 1 | * | 2 |

In conclusion, this comparative study of structure-function relationships in this small group of boronated porphyrins showed that the lipophilic, water-insoluble TPP's of this invention appeared the least toxic and delivered the greatest amounts of boron to tumor with the greatest tumor:normal tissue ratios.

BIBLIOGRAPHY

The following publications, mentioned in the foregoing specification, are incorporated herein by reference as if set forth in full for all they disclose:

CHIUSOLI, G. P., COSTA, M. and REVERBERI, S., Synthesis of pyrrole-3,4-diacetic acid and its derivatives, *Synthesis*, 262–265 (1989).

CODERRE, J. A., ELOWITZ, E., CHADHA, M., BERGLAND, R., CAPALA, J., JOEL, D. D., LIU, H. B., SLATKIN, D. N. and CHANANA, A. D., Boron neutron capture therapy of glioblastoma multiforme using p-boronophenylalanine and epithermal neutrons: Trial design and early clinical results. *J. NeuroOncol* 33, 141–152 (1997)

CODERRE, J. A., GLASS, J. D., FAIRCHILD, R. G., MICCA, P. L., FAND, I., and JOEL, D. D., Selective delivery of boron by the melanin precursor analogue p-boronophenylalanine to tumors other than melanoma, *Cancer Res.*, 50, 138–141 (1990).

FAIRCHILD, R. G., GABEL, D., LASTER, B. H., GREENBERG, D., KISZENICK, W., and MICCA, P. L., Microanalytical techniques for boron analysis using the $^{10}B(n, a)^7Li$ reaction. *Med. Phys.*, 13, 50–56 (1986)

MIURA, M., GABEL, D., OENBRINK, G. and FAIRCHILD, R. G., Syntheses of boronated porphyrins for boron neutron capture therapy. *Tetrahedron Lett.*, 31, 2247–2250 (1990).

MIURA, M., MICCA, P. L., FISHER, C. D., HEINRICHS, J. C., DONALDSON, J. A., FINKEL, G. C., and SLATKIN, D. N., Synthesis of a nickel tetracarboranylphenylporphyrin for boron neutron-capture therapy: Biodistribution and toxicity in tumor-bearing mice, *Int. J. Cancer*. 68, 114–119 (1996).

MIURA, M., MICCA, P. L., HEINRICHS, J. C., GABEL, D., FAIRCHILD, R. G. and SLATKIN, D. N., Biodistribution and toxicity of 2,4-divinyl-nido-o-carboranyl-deuteroporphyrin IX in mice, *Biochem. Pharm.*, 43, 467–476, (1992)

OENBRINK, G., JÜFRGENLIMKE, P. and GABEL, D., Accumulation of porphyrins in cells: Influence of hydrophobicity, aggregation and protein binding. *Photochem. Photobiol.*, 48, 451–456 (1988).

SLATKIN, D. N., Biodistribution and Toxicity of 2,4-divinyl-nido-o-carboranyl-deuteroporphyrins IX in mice, Erratum, *Biochem. Pharm.*, 50, 893–894 (1995).

Thus, while there have been described what are presently believed to be preferred embodiments of the present invention, those skilled in the art will realize that other and further modifications and changes can be made without departing from the true spirit of the invention, and it is intended to include all such changes and modifications as come within the scope of the invention as pointed out in the claims appended hereto.

We claim:

1. A compound of the formula

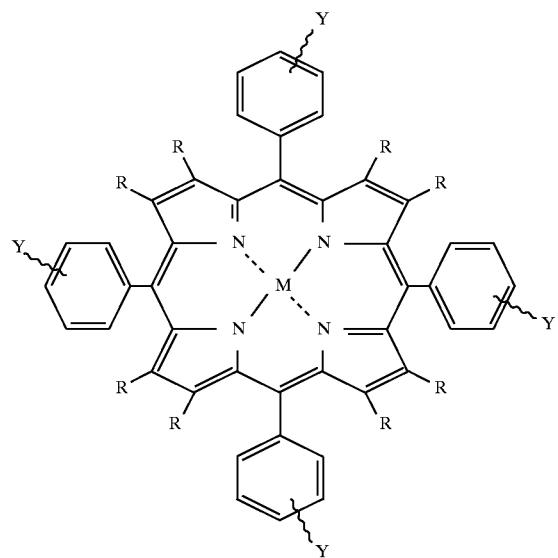

wherein M is 2H, or a SPECT imageable radiometal and/or a paramagnetic metal, R is H, alkyl or $(CH_2)_n COOZ$ when M is a metal or 2H, $0 \leq n \leq 20$; Z is selected from the group consisting of H, alkyl, or aryl; and Y is selected from the group consisting of ortho, meta, or para $O(CH_2)_n C_2 HB_9 H_{10}$ or $O(CH_2)_n C_2 HB_{10} H_{10}$ wherein, n is as defined above and $C_2 HB_9 H_{10}$ is nido ortho, meta-, or para-carborane and $C_2 HB_{10} H_{10}$ is ortho-carborane, meta-carborane or para-carborane, wherein whenever M is 2H or Zn, R is alkyl or $(CH_2)_n COOZ$.

2. A compound according to claim 1, wherein M is selected from the group consisting of V, Mn, Fe, Ru, Tc, Cr, Pt, Co, Ni, Cu, Zn, Ge, In, Sn, Y and Gd.

3. A compound according to claim 2, wherein M is Ni.

4. A compound according to claim 1, wherein R is $(CH_2)_n COOZ$.

5. A compound according to claim 4, wherein Z is alkyl.

6. The compound according to claim 5, wherein Z is methyl.

7. The compound according to claim 1, wherein R is $(CH_2)_n COOZ$ and n=1.

8. The compound according to claim 1, wherein Y is $OCH_2C_2HB_9H_{10}$ and wherein $C_2HB_9H_{10}$ is nido-ortho-carborane.

9. The compound according to claim 1, wherein Y is $OCH_2C_2HB_{10}H_{10}$ wherein $C_2HB_{10}H_{10}$ is ortho-carborane.

10. The compound according to claim 1, wherein M is Ni or Cu, R is $CH_2CO_2CH_3$, and Y is $OCH_2C_2HB_{10}H_{10}$.

11. The compound according to claim 1, wherein M is Ni or Cu, R is H and Y is $OCH_2C_2HB_{10}H_{10}$.

12. The compound according to claim 1, wherein alkyl is an unsubstituted straight chain or branched alkyl having 1 to 20 carbon atoms, aryl is unsubstituted phenyl, naphthyl or phenanthryl.

13. A compound of the formula

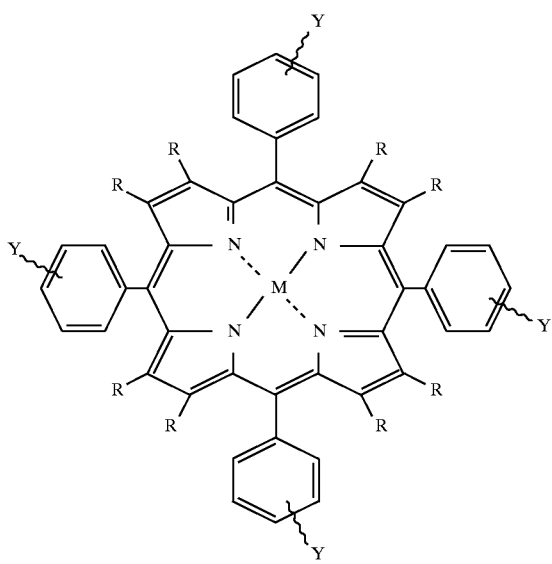

wherein M is 2H, or a SPECT-imageable radiometal and/or a paramagnetic metal, R is H, alkyl or $(CH_2)_nCOOZ$ when M is a metal or 2H, $0 \leq n \leq 20$; Z is selected from the group consisting of H, alkyl or aryl; and Y is selected form the group consisting of ortho, meta, or para $O(CH_2)_nC_2HB_9H_{10}$ or $O(CH_2)_nC_2HB_{10}H_{10}$, n is as defined above and $C_2HB_9H_{10}$ is nido ortho-carborane and $C_2HB_{10}H_{10}$ is ortho-carborane, meta-carborane or para-carborane, M is selected from the group consisting of V, Mn, Fe, Ru, Tc, Cr, Pt, Co, Ni, Cu, Zn, Ge, In, Sn, Y and Gd, wherein whenever M is 2H or Zn, R is alkyl or $(CH_2)_nCOOZ$.

14. A compound of the formula

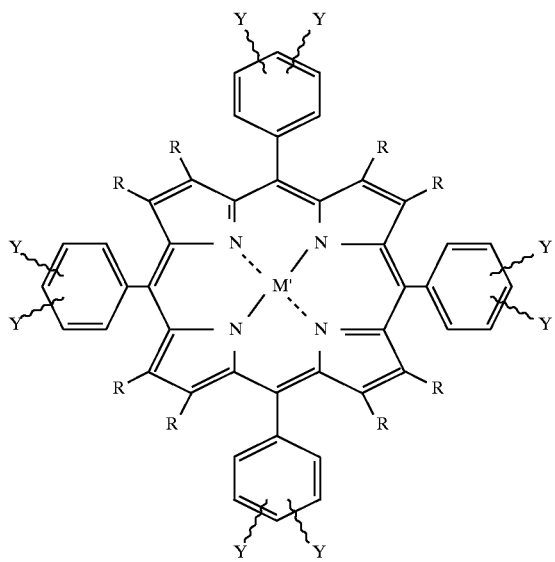

wherein $M^1$ is 2H, 4H, a SPECT-imageable radiometal or a paramagnetic metal; R is H, alkyl, or $(CH_2)_nCOOZ$, wherein $n \geq 0$ to 20, Z is selected from the group consisting of H, alkyl, or aryl; and Y is selected from the group consisting of ortho, meta, or para $O(CH_2)_nC_2HB_9H_{10}$ or $O(CH_2)_n C_2HB_{10}H_{10}$ wherein n is as defined above and $C_2HB_9H_{10}$ is nido ortho-carborane and $C_2HB_{10}H_{10}$ is ortho-carborane.

15. A method of treating malignant tumors comprising: administering to a person undergoing such treatment a therapeutically effective dosage of a compound of the formula

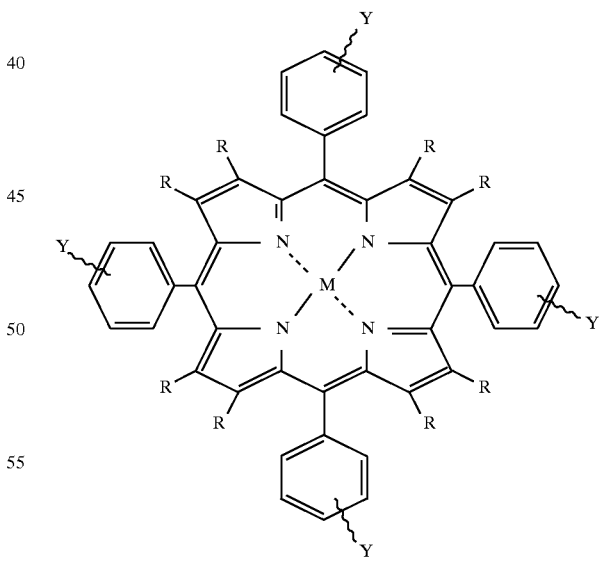

wherein M is 2H, or a SPECT-imageable radiometal and/or a paramagnetic metal, R, is H, alkyl or $(CH_2)_nCOOZ$ when M is a metal or 2H, $0 \leq n \leq 20$; Z is selected from the groupconsisting of H, alkyl or aryl; and Y is selected form the group consisting of ortho, meta, or para $O(CH_2)_nC_2HB_9H_{10}$ or $O(CH_2)_nC_2HB_{10}H_{10}$ wherein n is as defined above and $C_2HB_9H_{10}$ is nido ortho-carborane and $C_2HB_{10}H_{10}$ is ortho-carborane, meta-carborane or para-carborane, wherein whenever M is 2H or Zn, R is alkyl or $(CH_2)_nCOOZ$.

16. The method according to claim 13, wherein M is selected from the group consisting of V, Mn, Fe, Ru, Tc, Cr, Pt, Co, Ni, Cu, Zn, Ge, In, Sn, Y and Gd.

17. The method according to claim 15 wherein M is Ni.

18. The method according to claim 15, wherein R is $(CH_2)_nCOOZ$.

19. The method according to claim 18, wherein Z is alkyl.

20. The method according to claim 19, wherein Z is methyl.

21. The method according to claim 15, wherein R is $(CH_2)_nCOOZ$ and n is 1.

22. The method according to claim 15, wherein Y is $OCH_2C_2HB_9H_{10}$ and wherein $C_2HB_9H_{10}$ is nido ortho-carborane.

23. The method according to claim 15, wherein Y is $OCH_2C_2HB_{10}H_{10}$ wherein $C_2HB_{10}H_{10}$ is ortho-carborane.

24. The method according to claim 15, wherein M is Ni, Cu or Mn, R is $CH_2CO_2CH_3$, and Y is $OCH_2C_2HB_{10}H_{10}$.

25. The method according to claim 15, wherein M is Ni, Cu or Mn, R is H, and Y is $OCH_2C_2HB_{10}H_{10}$.

26. The method according to claim 15, wherein alkyl is an unsubstituted straight chain or branched alkyl having 1 to 20 carbon atoms, aryl is unsubstituted phenyl, naphthyl or phenanthryl.

27. The method according to claim 15, wherein said treatment of malignant tumors comprises boron neutron capture therapy.

28. The method according to claim 15, wherein said treatment of malignant tumors comprises photodynamic therapy.

29. The method according to claim 15, wherein said treatment of malignant tumors utilizes single-photon emission computerized tomography (SPECT) wherein M is any SPECT-imageable radiometal.

30. The method according to claim 15, wherein said treatment of malignant tumors utilizes magnetic resonance imaging (MRI) wherein M is any paramagnetic metal.

31. The compound of claim 1, wherein said compound is lipophilic.

32. The method of claim 15, wherein said compound is lipophilic.

* * * * *

UNITED STATES PATENT AND TRADEMARK OFFICE
CERTIFICATE OF CORRECTION

PATENT NO. : 5,877,165

DATED : March 2, 1999

INVENTOR(S) : Michiko Miura, et al.

It is certified that error appears in the above-identified patent and that said Letters Patent is hereby corrected as shown below:

On the title page, item [54] and column 1

The word "PORHYRINS" in the title of the issued patent should be corrected to read --PORPHYRINS--.

Signed and Sealed this

Thirteenth Day of July, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,877,165
DATED : March 2, 1999
INVENTOR(S) : Michiko Miura, et al.

It is certified that error appears in the above-identified patent and that said Letters Patent is hereby corrected as shown below:

The above-identified U.S. Patent 5,877,165 is a Continuation-In-Part application of abandoned U.S. Patent Application S.N. 08/552,148 filed 11/2/95. Enclosed is copy of Combined Declaration and Power of Attorney, as filed at U.S. Patent and Trademark Office, showing on Page 7 the added page for a Continuation-In-Part application.

Signed and Sealed this

Twenty-eighth Day of September, 1999

Attest:

Q. TODD DICKINSON

*Attesting Officer*     *Acting Commissioner of Patents and Trademarks*